(12) United States Patent
Radaelli et al.

(10) Patent No.: US 10,561,518 B2
(45) Date of Patent: Feb. 18, 2020

(54) WEARABLE SUPPORT STRUCTURE AND METHOD OF SUPPORTING A TORSO

(71) Applicant: Laevo B.V., Delft (NL)

(72) Inventors: Giuseppe Radaelli, Delft (NL); Emile Johannes Rosenberg, Delft (NL); Milton Edward Aguirre, Delft (NL); Anna Christina Verkuyl, Delft (NL); Boudewijn Martin Wisse, Delft (NL)

(73) Assignee: LAEVO B.V., Delft (NL)

( * ) Notice: Subject to any disclaimer, the term of this patent is extended or adjusted under 35 U.S.C. 154(b) by 717 days.

(21) Appl. No.: 15/022,594

(22) PCT Filed: Sep. 19, 2014

(86) PCT No.: PCT/NL2014/050646
§ 371 (c)(1),
(2) Date: Mar. 17, 2016

(87) PCT Pub. No.: WO2015/041532
PCT Pub. Date: Mar. 26, 2015

(65) Prior Publication Data
US 2016/0250062 A1    Sep. 1, 2016

(30) Foreign Application Priority Data

Sep. 20, 2013 (NL) ........................... 2011482
Sep. 20, 2013 (NL) ........................... 2011483

(51) Int. Cl.
*A61F 5/02* (2006.01)
*A61F 5/01* (2006.01)

(52) U.S. Cl.
CPC .............. *A61F 5/026* (2013.01); *A61F 5/028* (2013.01); *A61F 2005/0179* (2013.01)

(58) Field of Classification Search
CPC .. A61F 5/026; A61F 5/02; A61F 5/028; A61F 2005/0179; A61F 5/0123;
(Continued)

(56) References Cited

U.S. PATENT DOCUMENTS

| 443,113 A | 12/1890 | Ray |
| 654,173 A | 7/1900 | Mendenhall |

(Continued)

FOREIGN PATENT DOCUMENTS

| DE | 44 18 806 | 12/1995 |
| DE | 196 52 416 | 6/1998 |

(Continued)

OTHER PUBLICATIONS

International Search Report dated May 28, 2014 for NL 2011483.
(Continued)

*Primary Examiner* — Ophelia A Hawthorne
(74) *Attorney, Agent, or Firm* — Pillsbury Winthrop Shaw Pittman, LLP

(57) ABSTRACT

The invention relates to a wearable support structure for at least partly relieving a human body during leaning forward or bending over. The wearable support structure comprises a frame having at least one stay provided with a chest support for bearing upon a chest area, a lumbar support for bearing upon a lumbar area, and a thigh support for bearing upon a front side of a thigh area. The stay is a flexible stay arranged such that it is in a stretched state corresponding with an upright position of a human body when being unloaded. Further, the stay is arranged to be biased back to said stretched state when being bent into a bent state corresponding with a forward leaning position of a human body.

42 Claims, 21 Drawing Sheets

(58) Field of Classification Search
CPC ............ A61F 5/0585; A63B 21/00181; A63B 21/4025; A61H 3/00
See application file for complete search history.

(56) References Cited

U.S. PATENT DOCUMENTS

| | | | |
|---|---|---|---|
| 1,371,690 | A | 3/1921 | Kelly |
| 4,829,989 | A * | 5/1989 | Deamer ............... A61F 5/02 602/19 |
| 5,176,622 | A | 1/1993 | Anderson et al. |
| 5,782,781 | A * | 7/1998 | Nagaoka ............ A61F 5/028 128/101.1 |
| 5,816,251 | A | 10/1998 | Glisan |
| 6,450,131 | B1 | 9/2002 | Broman |
| 6,471,665 | B1 * | 10/2002 | Milbourn ............ A61F 5/024 128/103.1 |
| 7,744,552 | B1 | 1/2010 | Babcock |
| 9,744,066 | B2 * | 8/2017 | Kazerooni ........... A61F 5/028 |
| 2009/0095308 | A1 * | 4/2009 | Mckinney ........... A61F 5/026 128/870 |
| 2010/0069806 | A1 | 3/2010 | Jinright et al. |
| 2011/0098617 | A1 | 4/2011 | Ferguson et al. |
| 2013/0131560 | A1 * | 5/2013 | Ferguson ............ A61H 3/00 601/33 |
| 2016/0128861 | A1 * | 5/2016 | Plaza ................. A61F 5/028 602/19 |

FOREIGN PATENT DOCUMENTS

| | | |
|---|---|---|
| DE | 10 2004 008 509 | 11/2004 |
| DE | 20 2009000076 | 4/2010 |
| EP | 0 181 688 | 5/1986 |
| EP | 1264583 | 12/2002 |
| JP | 09-00552 A | 1/1997 |
| JP | 2009-023828 A | 2/2009 |
| JP | 2011-188896 A | 9/2011 |
| WO | WO 95/35075 | 12/1995 |
| WO | WO2007/107952 | 9/2007 |
| WO | WO 2008/125802 | 10/2008 |

OTHER PUBLICATIONS

International Search Report dated Dec. 16, 2014 for PCT/NL2014/050646.
Notification of Reasons for Refusal issued in corresponding Japanese Patent Application No. 2016-544306 dated Nov. 13, 2018 with English translation.
Notice of Reasons for Refusal dated Sep. 24, 2019 issued in corresponding Japanese Patent Application No. 2016-544306 with English translation.

* cited by examiner

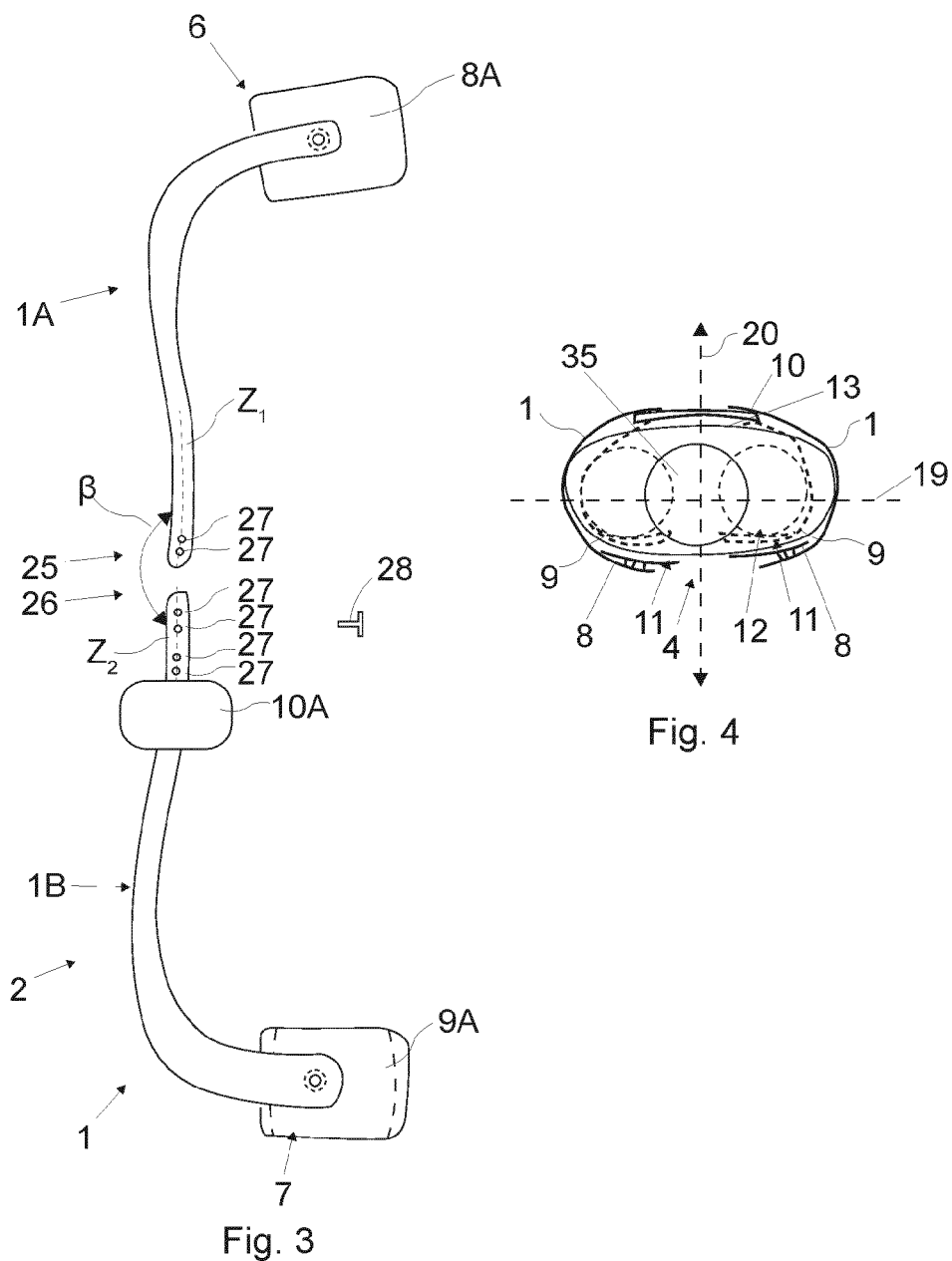

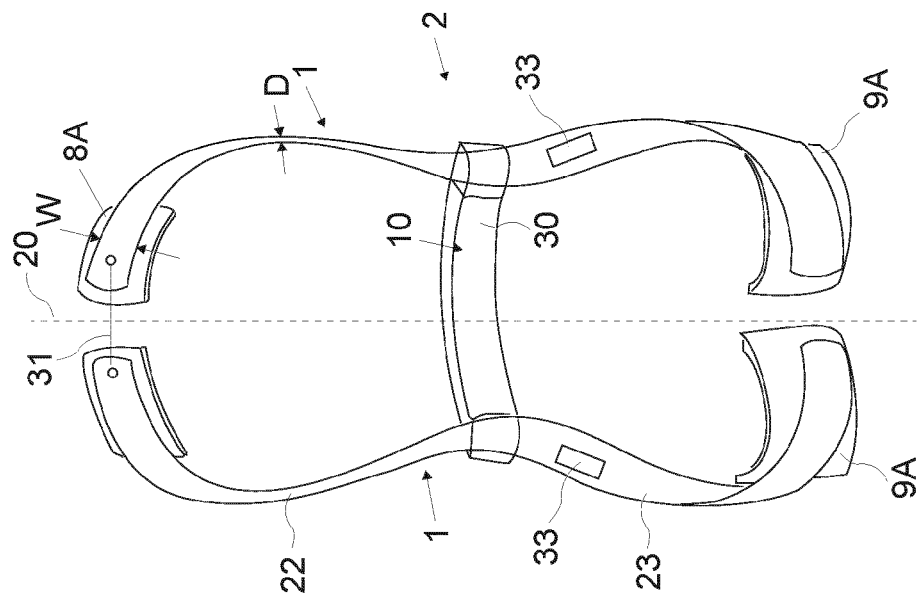
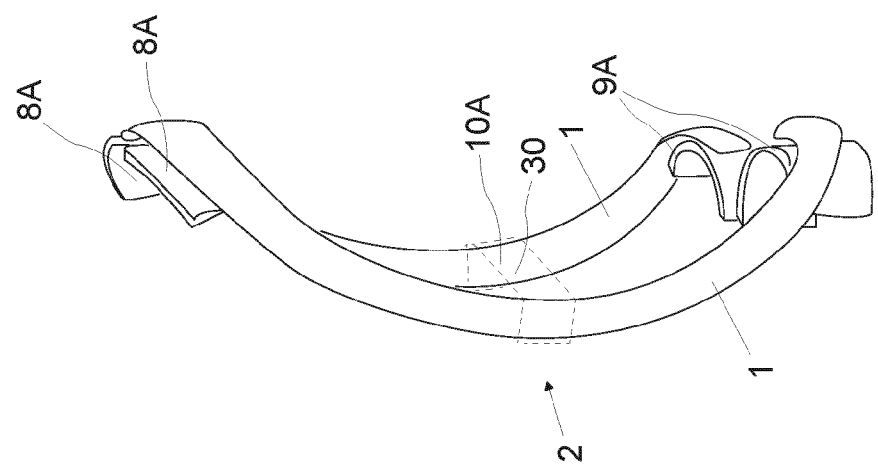
Fig. 7

WEARABLE SUPPORT STRUCTURE AND METHOD OF SUPPORTING A TORSO

CROSS-REFERENCE TO RELATED APPLICATIONS

This is the U.S. National Stage of PCT/NL2014/050646, filed Sep. 19, 2014, which in turn claims priority to Netherlands Application Nos. 2011483, filed Sep. 20, 2013, and U.S. Pat. No. 2,011,482, filed Sep. 20, 2013. The entire contents of all applications are incorporated herein by reference in their entireties.

The invention relates to a wearable structure for supporting a body part. The invention relates to a wearable structure for relieving at least in part a human body during leaning forward or bending over. Such structure is for example known from the patent publication U.S. Pat. No. 1,371,690 from 1921.

When bending over, such as during leaning forward, the skeleton and muscles of a person are strained far more than when standing straight. This is even further worsened when for example lifting a load or otherwise performing a task in such bent position. Especially when staying in such position for a prolonged period of time this may be detrimental to the body.

In U.S. Pat. No. 1,371,690 a support structure is described which can be worn on the body to support part of the body, especially the upper body, when bending over. In this structure a frame structure is provided with a shoulder portion and a leg portion, connected by a bendable strip and a spring. The shoulder portion can be supported over the shoulders of the person wearing it, and the leg portion comprises to leg supports which can each be attached to an upper leg. Straps are provided for attaching the shoulder portion to the torso over the chest and for strapping the leg supports to the legs. The spring is connected between a lower end of the strip, extending from the shoulder portion, and the leg portion. Upon bending of the body the shoulder portion will follow the shoulders, thus bending the strip and stretching and bending the spring. Thus a force is obtained working in the direction opposite to the bending. In other words the structure will provide for a supporting force for the upper body.

This known structure has proven to be uncomfortable for the person wearing it, is cumbersome to attach and moreover has a force pattern which changes uncomfortably and erratically when bending, for example depending on the positioning of the structure, the body properties of the person, such as shape, body weight and weight distribution, available space between the strip and spring on the one hand and the body, especially lumbar region and back on the other hand and body flexibility. Moreover this structure may impair a person in his freedom to move, especially in moving his or her arms. Although there is a long-felt need to improve this known structure, other known structures and devices are still not able to overcome the problems and disadvantages associated with such structures.

EP1264583 discloses a structure for supporting the body in which over the legs and back of a person a construction of elastic straps is provided, connected to the ankles, lower back and shoulders. A further provision can be provided around the thigh. A similar construction is known from U.S. Pat. No. 6,450,131. Similar constructions are known from for example U.S. Pat. No. 654,173 and U.S. Pat. No. 5,816,251, both having the lower end of the structure attached by straps around the thighs, which will be pulled up into the crotch area. These known structures are uncomfortable, cumbersome to apply and provide at best sub-optimal support.

US 2009/0095308 discloses a support device or brace device that limits the movement of the spine in order to encourage proper ergonomic lifting techniques. No lumbar support is disclosed and no thigh supports are disclosed.

US2010/0069806 discloses a brace comprising a rigid frame provided with a chest pad, a lumbar pad and thigh pads. Said brace is specifically designed to achieve an upright posture for patients that suffer from having a forward lean due to spinal weakness. The brace is arranged to prevent patients to lean forward and does thus not provide for a wearable structure for relieving at least in part a human body during leaning forward or bending over.

WO2007/107952 discloses an apron provided with super elastic components extending at the front side of a human body during use of the apron. The super elastic components extend over the front side of the human body from a chest area, via the belly of a person towards the thigh area. No lumbar support is disclosed. A problem of these super elastic components can be that, when a user bends over or leans forward, the lower ends thereof can slide downwards over the thighs of a user and/or that the upper ends thereof can slide upwards towards a users throat.

U.S. Pat. No. 5,176,622 discloses a stoop labor assist device comprising a belt to which two spools are attached at a location in alignment with the normal flexion center of rotation of the human body. The device further comprises a frame. Said frame has a rigid upper torso engaging portion with a chest pad. The frame further comprises two rigid tubes at their lower ends provided with a thigh pad and at their upper ends connected to two lower ends of the upper torso engaging portion of the frame by means of two arcuate springs, which two springs can be snapped around the spools of the belt. One of the disadvantages of this device lays for instance in the fact that fitting the belt on and positioning the spools at the right spots is a cumbersome and error prone process.

WO2008/125802 discloses a body support apron. The apron comprises a flexible sheet of textile material housing two spring elements which act to flex the apron sheet back to its straight position when a user bends forward. This device is uncomfortable and provide at best sub-optimal support.

U.S. Pat. No. 443,113 discloses a support structure having a shoulder support, leg supports and a lumbar support, connected by resilient rods extending alongside the sides of the body. The upper ends of the rods are connected to the shoulder support at the back of the body, as are the lower ends of the rods to the leg supports. The lumbar support is formed by a strap pulling the mid section of the rod backward. Again such structure is uncomfortable, especially since both the shoulders and the legs are pulled rearward and the freedom of movement of the arms and legs is limited, is cumbersome in structure and use and does not provide adequate support. Moreover, bending becomes increasingly more difficult when bending more forward.

DE202009000076 discloses a support structure having upper and lower frame parts, pivotally connected to each other by pivots comprising springs biasing the structure to a straight position. The upper and lower parts are rigid. A strap is provided for strapping the upper part to the chest. Leg supports are provided to the lower part. No lumbar support is disclosed.

U.S. Pat. No. 7,744,552 discloses a wearable support for supporting a body part, especially an upper body part when bending over. This support structure comprises a central hollow tube extending across over the ventral area of the person wearing the structure. Within the tube a torsion spring mechanism is provided connecting at opposite lateral ends to two arms releasable connected to the torsion mechanism and extending downward. Each one of these arms comprises a hinge directly below the tube allowing the arm to pivot in a plane including the arms and the tube axis. Each arm is at a lower free end provided with a thigh support. From the tube a support structure extends upward, which carries a chest support at it's free end. Moreover a ventral support is provided comprising two eyelets surrounding the tube. A waist band is provided which can be connected to the ventral support, for attaching the structure to the person using the structure. The structure thus supports the upper body through the torsion spring mechanism and the thigh supports resting on the upper legs. These thigh supports with the attached arm can move independently of each other. This support structure is relatively heavy, due to i.a. the tube and torsion spring mechanism and needs to be fixed to the body by the waist band. Moreover, the ventral area of the person wearing the structure is not free, due to the tube. Furthermore upon bending of the body the chest support will be moved relative to the chest and upper body, since there is a fixed distance between the tube and chest support. This is uncomfortable and moreover leads to changing positions of where a support force works on the upper body and support which may feel unpredictable to a wearer. Similarly the thigh supports will change position relative to the leg, due to the fixed distance between the tube and the thigh supports.

An aim of the present invention is to provide for an alternative support structure for a body part, especially an upper body part.

An aim of the present invention is to provide a wearable support structure which alleviates at least in part some or all of the problems and disadvantages of the known structures.

An aim of the present invention is to provide a wearable support structure which allows a person wearing the structure to receive ample support from the structure and at the same time allow him or her sufficient freedom to move, especially to move the arms during for example bending or in a bent position.

An aim of the present invention is to provide a wearable support structure which allows easy mounting and dismounting of the structure onto and from the body by a wearer.

An aim of the present invention is to provide a wearable support structure which can be worn under clothing, such as under a coat, shirt or the like.

An aim of the present invention is to provide a wearable support structure which has a well defined profile in forces exerted onto the body of a person wearing the structure and/or a well defined and maintained position relative to the body of the wearer in different positions of the body, especially when bending.

An aim of the present invention is to provide a wearable support structure which, when worn on a human body, provides a supporting force to an upper part of the body when bending over, which may vary depending on the angle of bending, over part or all of the trajectory over which the body can bend.

At least one of these and/or other aims and objects of the present invention can be obtained at least in part by a wearable structure according to this description. Different aspects of the present disclosure shall be briefly discussed here after in no particular order, unless otherwise specified.

In an aspect of the disclosure, a wearable support structure can comprise a frame having at least one stay provided with a chest support for bearing upon a chest area, a lumbar support for bearing upon a lumbar area, and a thigh support for bearing upon a front side of a thigh area. The stay preferably is at least partly flexible. The at least one stay can be arranged such that it is in a stretched state or so-called relaxed state when worn on a human body with the human body in a relaxed position, and arranged to be biased back to said stretched state when being bent into a bent state corresponding with a forward leaning position of a human body.

In other words, when the stay is bent from its stretched state into a bent state, it will be biased to regain its stretched state. It is noted that the stretched state or so-called relaxed state can correspond to a relaxed position of the human body, such as for instance an upright position. The upright position may be a so-called standing position of the human body or a sitting position of the human body. For example, the relaxed state can correspond to a relaxed position of a bent human body in which an angle between the upper body and the upper leg can be between 80 and 140 degrees, e.g. about 90 to 120 degrees, seen in a sideward direction. In case of a standing position, the angle can be e.g. between 170 and 210 degrees, for instance substantially 180 degrees.

By making the stay at least partly flexible, it may be facilitated that a user wearing the structure has a relatively large freedom of movement, while at the same time the structure can support at least a part of the load of an upper body when the user bends forward, thereby partly relieving the back of the user. For instance, an at least partly flexible stay can facilitate that the user can twist his body about its longitudinal axis to at least some extent, e.g. both while a user stands upright and while a user bends/leans forwards. Additionally or alternatively, an at least partly flexible stay can facilitate that the user can flex laterally to at least some extent, e.g. both while a user stands upright and while a user bends/leans forwards.

By making the stay at least partly flexible, it may additionally or alternatively be facilitated that the shape of the structure and/or its stay(s) can follow the movement and/or (changing) shape of the spinal column in a relatively natural way. In contrast to a pivotable frame with substantially rigid stays, a structure with one or more at least partly flexible stays can counteract in an elegant manner that an upper portion of the structure, e.g. a chest support, can slide upwardly unintentionally and/or that a lower portion of the structure, e.g. a thigh support, can slide downwardly unintentionally. By counteracting such undesirable shifting of the supports, e.g. of its support(s), a structure can be provided which is relatively comfortable and/or reliable in use.

In an aspect the wearable support structure can comprise two stays, preferably mirror imaged relative to an intermediate plane which corresponds to the sagittal plane when the structure is worn by a user.

Advantageously, the or each stay can be arranged such that when the user wearing the structure bends forwardly from his upright position towards a position including a first angle, the flexible stay provides for an increasing biasing moment biasing the flexible stay back to the stretched state of the stay and when bending further forwardly from the said angle the biasing moment provided by the stay is substantially maintained or decreases. As a result, the structure can substantially correspond to a gravity characteristic corresponding to an inverted pendulum, which preferably can approach a gravity characteristic of a human upper body leaning forwardly relatively well.

Preferably the or each stay extends from a frontal chest area alongside a side of the torso, below the relevant armpit towards a side and/or rear lumbar area and then alongside the hip and/or upper leg towards a frontal and/or inner thigh area, such that when the torso and leg are brought closer to each other, in other words when the body is bent, in the sagittal and/or the coronal plane, the at least one stay is flexed at least in part elastically, exercising a force onto the body back towards an upright position.

In an aspect the at least one stay can be substantially strip shaped, having a three-dimensional curved shape, the strip having for example a flat, curved, triangular or multi angular, round or oval cross section, which may be constant over the length of the stay or can vary along said length. A structure according to the disclosure can comprise padding or other support elements for resting against the body, between a stay and the body, for providing a more even spreading of forces exerted by the stay on the body and vice versa and providing for improved comfort, especially when the stay is made of a relatively hard material, such as plastic and/or metal. Advantageously the at least one stay has a curved shape, especially a curved shape being arranged to fit or follow body curves of the human body.

When two stays are provided, for fitting to a right and left side of the body respectively, the stays may be connected to each other, for example at, near and/or by the chest support or supports and/or at, near and/or by the lumbar support or supports, for example releasably. In embodiments the connection or connections can be provided such that the structure can be mounted to a body from the front and closed around the body be connecting the stays in the lumbar area, or mounted from the rear if desired closed at the front, for example in the chest area, such as by means of two interconnectable chest supports or chest pads.

In embodiments the leg support or supports can be fitted onto the legs without having to be strapped or clamped into position. In embodiments the chest support or supports can be placed against the chest area without having to be strapped and/or clamped into position. Preferably in a structure according to the disclosure the stomach area of the body is kept free from the structure, such that bending of the body in the lumbar back region is even more easily possible in all directions.

Moreover preferably the structure allows rotation of the upper body relative to the legs and/or hips as well.

By providing the at least one stay alongside a body and more preferably two stays alongside opposite sides of the body, the structure can allow such rotation especially well, whereas bending of the body in different directions, e.g. twisting the human body about its longitudinal axis, is still possible and will lead to the supporting function of the upper body part.

By arranging the structure in such a manner that the at least one stay extends alongside the body or two stays extend alongside opposite sides of the body, the structure can be relatively advantageous. For example, relative shortening of the front side of the human body, i.e. shortening of the distance between the thigh or upper leg and the chest, due to bending forward can cause that a structure extending at the front side of a human body can for instance slide upwardly towards a user's neck or throat. However, in case of an inventive structure of which the stay or stays extends alongside the body, it can be counteracted that upper parts of the structure, e.g. a chest support, will slide upwardly. By providing the stay alongside the human body, it can be facilitated that the stay can substantially follow the movement and/or (changing) shape of the spinal column.

Especially in embodiments, wherein the at least one stay extends alongside the body or two stays extend alongside opposite sides of the body, and wherein the stay is further at least partly flexible, it can be facilitated relatively well that the stay can substantially follow the movement and/or (changing) shape of the spinal column.

In embodiments at least one and preferably each of the supports are connected to the respective stay by means of a substantially pivotable connection, preferably substantially pivotable in two planes at the same time, so as to enable the support to fit the human body and/or distribute the pressure more equally when the stay is bent. The supports can be connected to the stay by a pivotable connection, such as a ball coupling or multi-axes hinge. In preferred embodiments the connection comprises or is formed by a flexible element such as a rubber of elastomer element. Preferably the connection is designed such that the relevant support is biased to a position in which the support fits against a relevant body part of the body when the relevant stay is in the stretched position.

In an aspect of the present disclosure a set of a wearable support structure and a piece of clothing can be provided, such as a coat or shirt, which can be connected with the support structure, such as with the stay or stays. The piece of clothing and the stay can to that end be provided with suitable connecting means, such as Velcro type means, magnetic means, push button connectors, clips or the like, or the piece of clothing can be provided with pockets, straps or the like for receiving part of the or each stay. Preferably the set is designed such that by putting on the piece clothing the support structure connected to it will be fitted properly to the body. The piece of clothing can be arranged to keep the wearable support structure in place during use. The set and/or structure can be arranged to be suspended from the human body at least partly by one or more pieces of clothing connected and/or connectable therewith. As a result, the structure can be kept in place relatively easily and/or it counteracted that the structure can slip down, e.g. in a relaxed state of the structure. Preferably the structure is covered at least substantially and more preferably entirely by the piece of clothing. Obviously several pieces of clothing can be combined for this purpose. As a result, the piece of clothing can be kept in place relatively easily and/or it can be facilitated to put on said set. Additionally or alternatively, it can enable that the wearable support structure can be hidden from view to at least some extent, which may increase the acceptation of the wearable support structure and/or the set by its wearer and/or may counteract scaring people, such as patients.

In an aspect the disclosure can be directed to a method for supporting part of a human body, wherein at least one at least partly flexible stay is mounted on the body, such that the stay is supported at least on a frontal chest area, a rearward lumbar area and a forward and/or inner thigh area. The stay is preferably clamped against said areas when the body is in an upright position at least by elastic deformation of at least part of the stay, and wherein the stay is deformed elastically by the wearer when bending his body forward and/or sideways, such that the upper part of the body is supported by the at least one stay.

In an aspect embodiments according to the present disclosure the structure or set can be provided with at least one sensor for registering movements of at least part of a body, which can for example be sensed by deformations of and/or strains in the structure, such as in and/or of the at least one stay. Data gathered by such sensor or sensors can be used for example for job evaluations, valuation and/or optimization of support tasks, work environments, tracking of tasks and the like.

In an aspect embodiments of a structure according to the present disclosure can comprise at least one pivoting arrangement between an upper and lower stay part or stay parts, with a biasing provision biasing the stay or stays towards a stretched position. The biasing provision or biasing means can be or comprise a resilient element connected to the upper and lower stay parts spaced apart from a pivot axis between the upper and lower stay parts. The pivot arrangement can be arranged such that when the upper and lower stay parts are pivoted around the pivot axis from a stretched position to a position including a first angle, the biasing means provide for an increasing biasing moment biasing the stay back to the stretched position and when pivoting further around said pivot axis from the said angle the biasing moment is substantially maintained or decreases.

It is noted that the stay may be arranged such that it cannot bend further backwards than the stretched position when it is being bent back by the biasing means. For instance, the structure can be provided with one or more stops for counteracting that the stay can pivot backwards, i.e. enabling that the stay can only bend forward with respect to its stretched position. In embodiments, the biasing means such as the resilient element can be arranged such as to be biased when the stay is in the stretched position. The biasing means may be biased to tend to pull the upper stay part backwards with respect to the lower stay part, when the stay is in its stretched position, while the stop or stops counteract that the stay parts rotate backwards with respect to each other.

The or each stay including an upper stay part and a corresponding lower stay part, including if applicable the or each biasing provision, is preferably such that in a first trajectory of pivoting of the or each relevant stay and/or bending of a body at the hip region of a person wearing the structure the biasing moment will increase, wherein in a second trajectory of pivoting of the or each relevant stay and/or bending of the body and/or when squatting said biasing moment will be kept equal or preferably will be reduced, for instance will be reduced even to substantially zero. This results in that in said first trajectory a positive support for the upper body is given when bending forward, whereas in the second trajectory the person wearing the structure is not or to only a limited extend hindered by the structure. This means that for such person for example picking something up from a floor or such lower position by bending over will still be relatively easy, whereas he will be provided ample support when bending forward over the first trajectory, reducing strain on muscles and/or ligaments and the skeleton. Additionally, such structure may accomplish that a person bending over to some extent in the in the first trajectory of pivoting can experience a comparable positive support substantially regardless of the bending angle in said first trajectory. The structure can thus provide for a plurality of consecutive positive support positions in a working area in the first trajectory, whereas conventional structures can provide for only one supporting position when a person bends forward.

Further aspects are described in the further description and claims. Two or more of the above described features and aspects of the present disclosure can be combined in any embodiments of the present disclosure.

Embodiments of the present invention shall be described, with reference to the drawings, for elucidation of the invention. These embodiments should by no means be understood as limiting the scope of the invention in any way or form. In these drawings:

FIG. 3 is a schematic perspective frontal view of a first alternative embodiment of a stay;

FIG. 4 is a schematic top view of person wearing a structure according to the disclosure, over a piece of clothing, especially a coat;

Figure 5A:
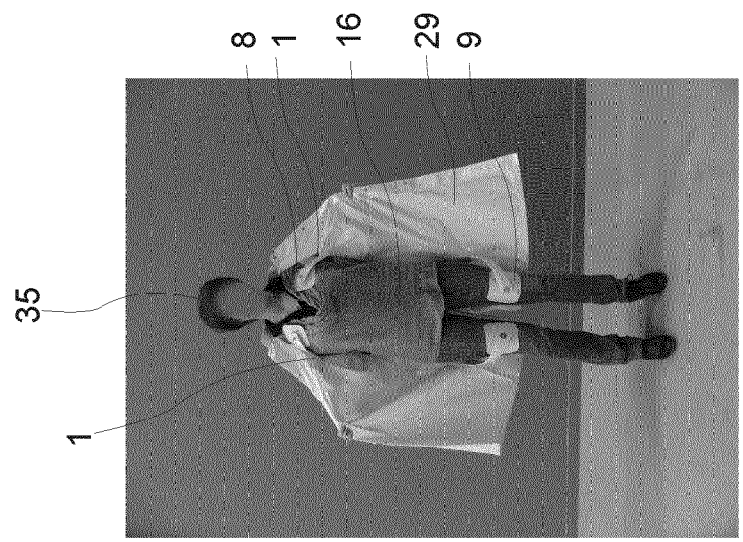
Figure 6:
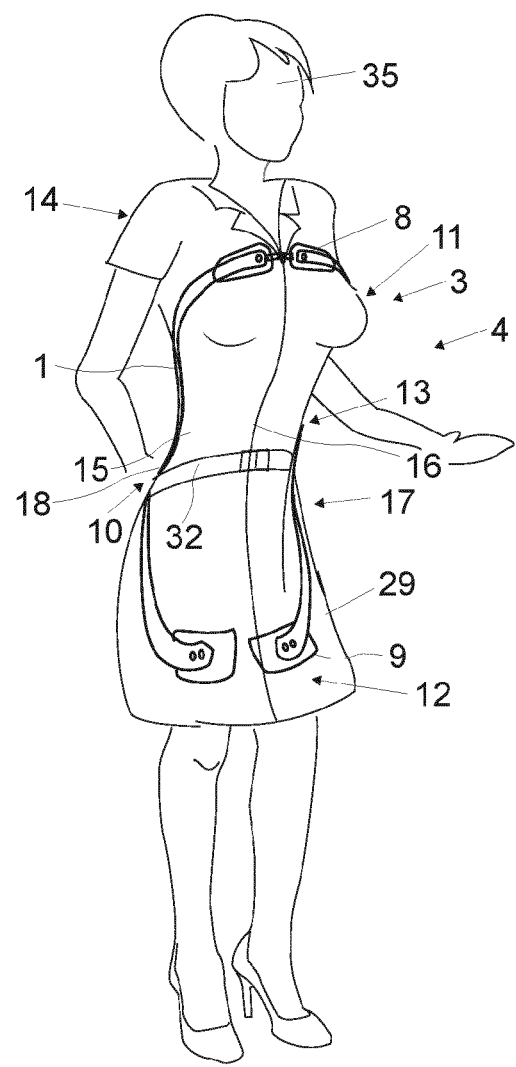
Figure 8:
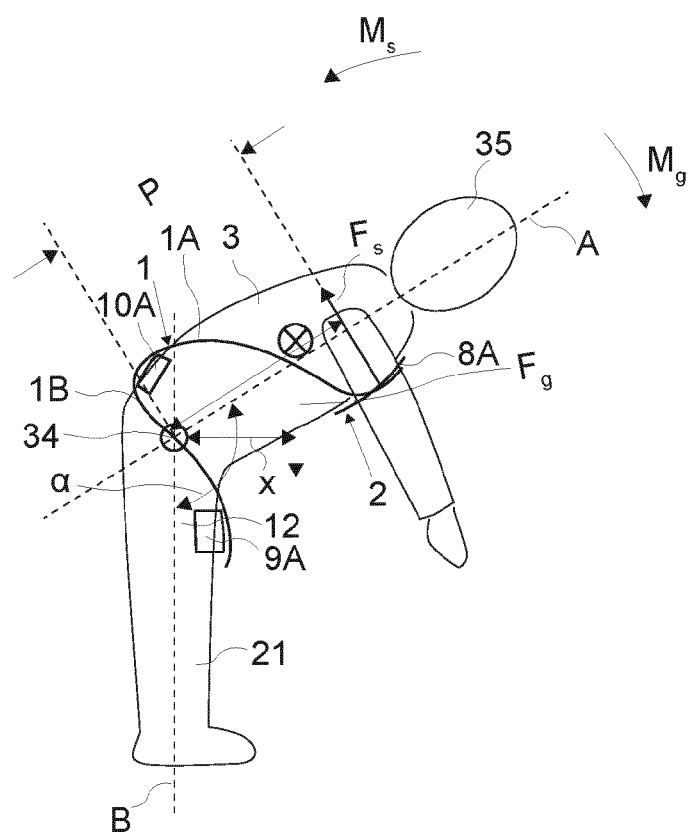
Figure 9:
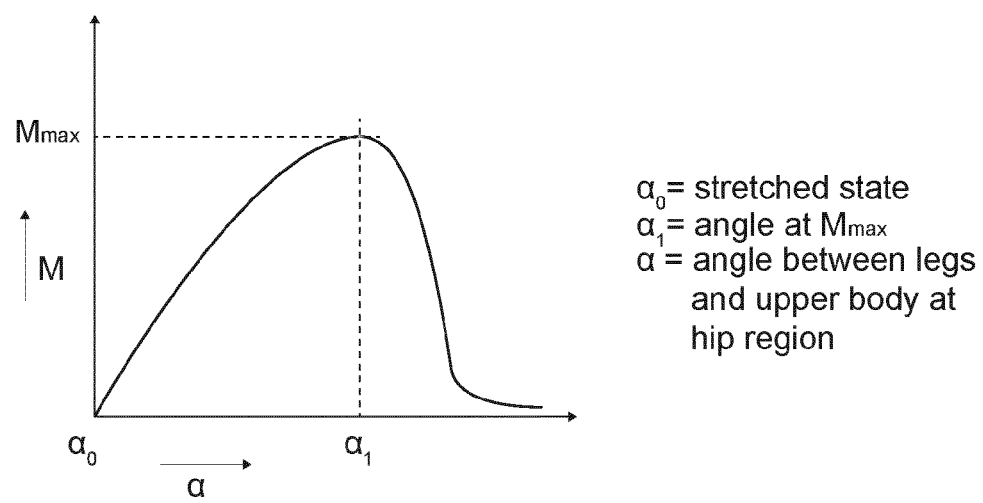
Figure 10:
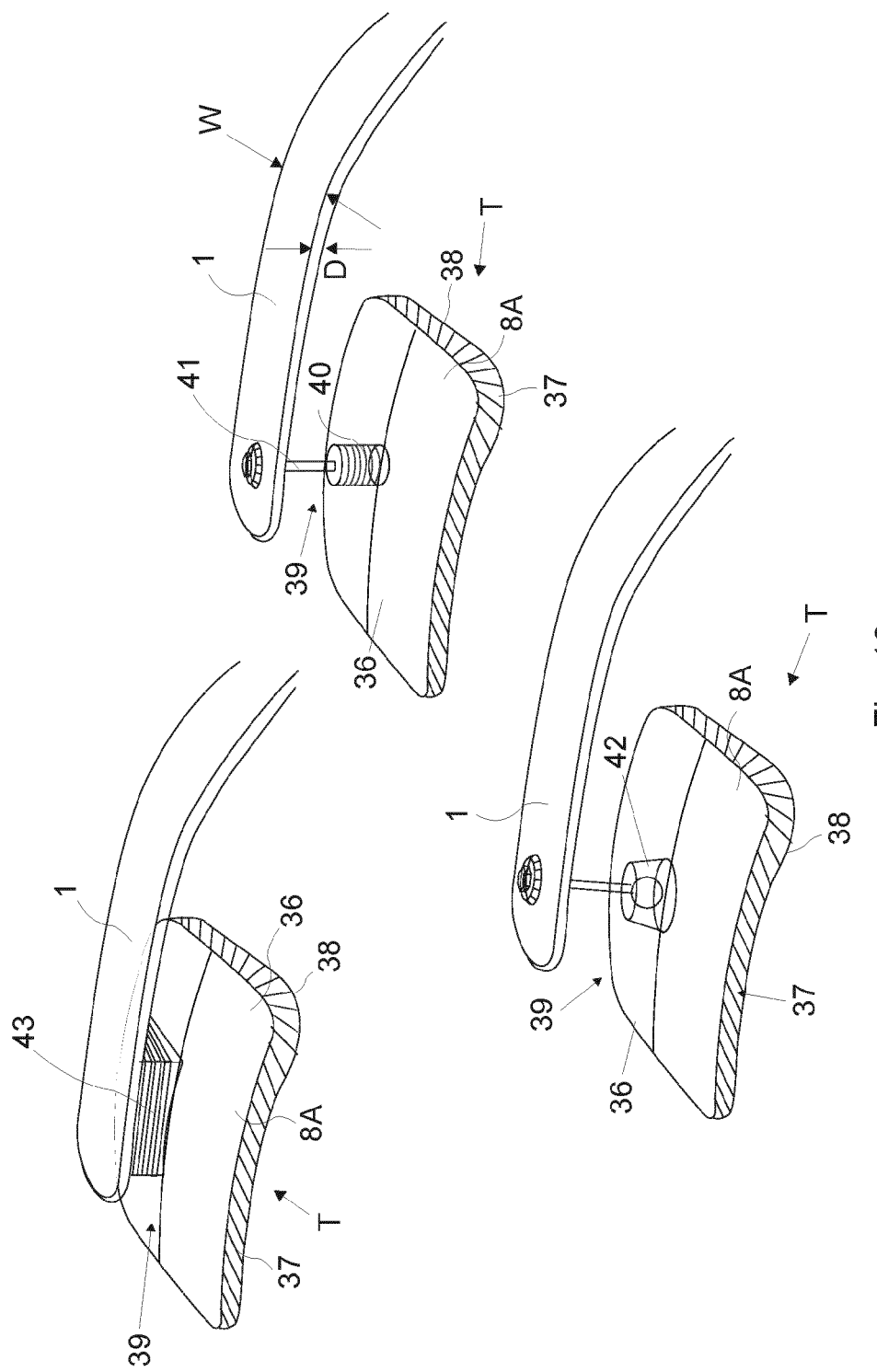
Figure 11:
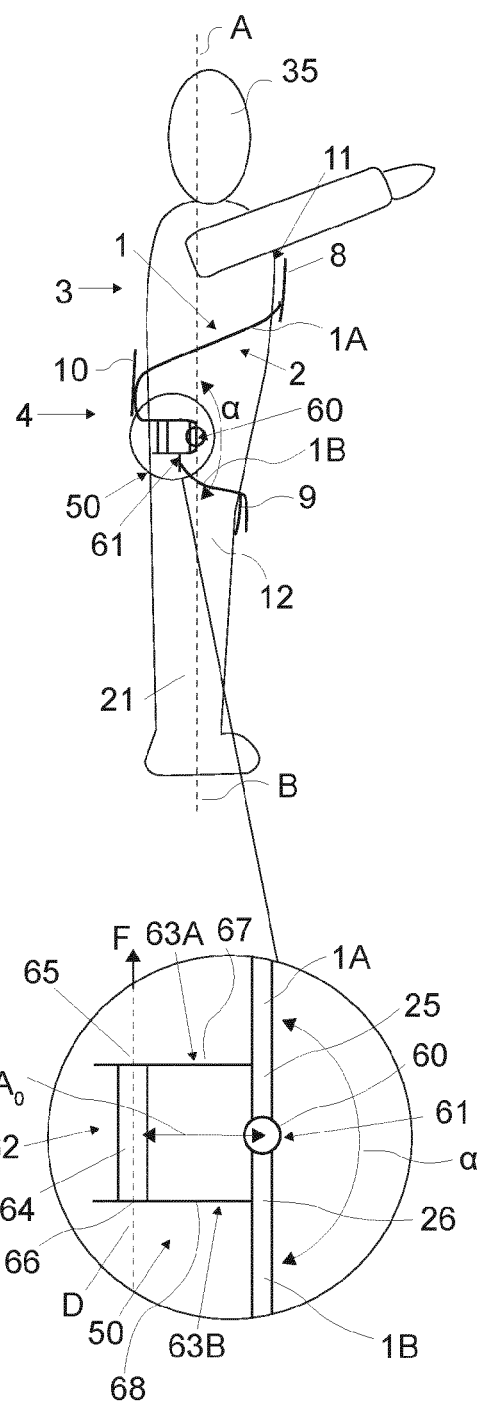
Figures 12A, 12B:
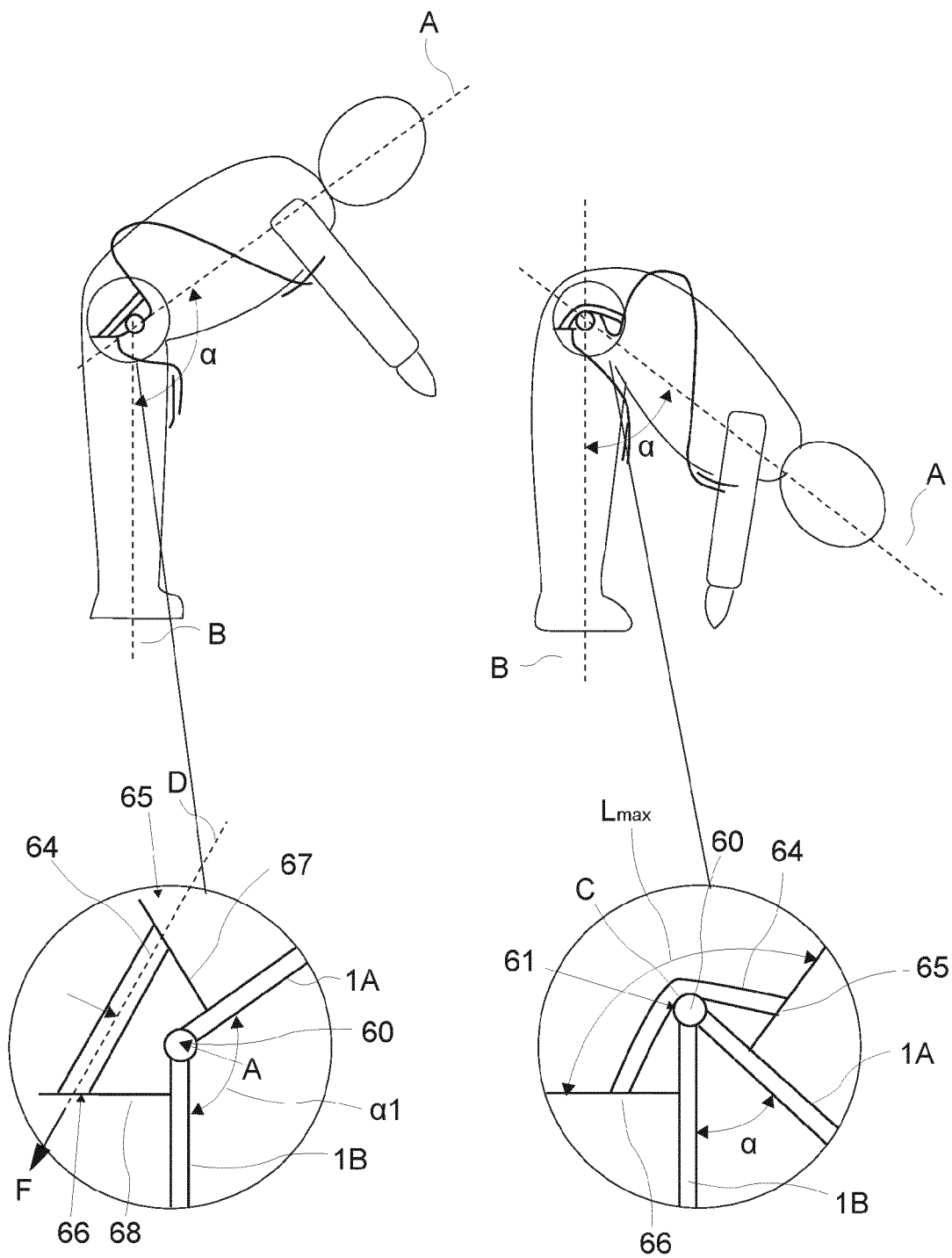
Figure 13:
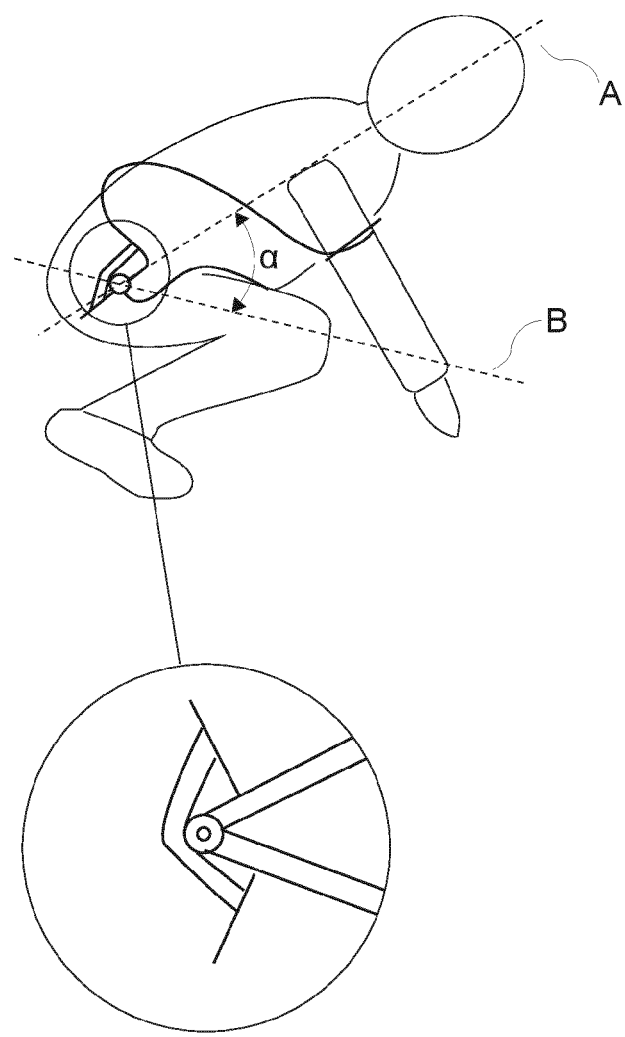
Figure 14:
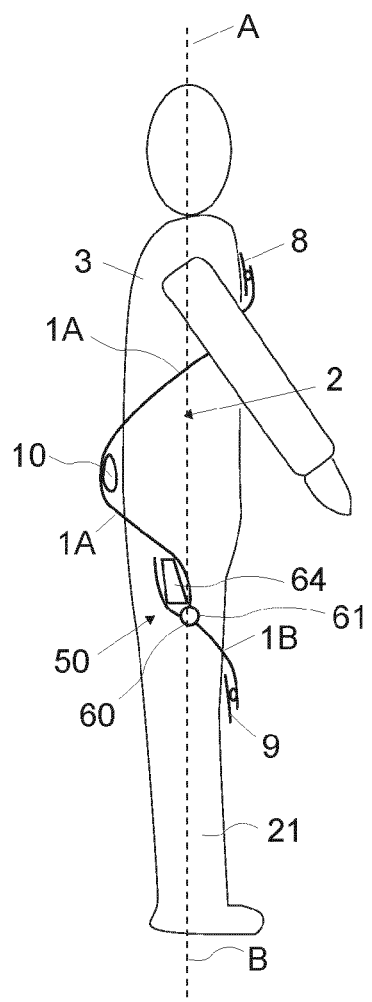
Figure 15:
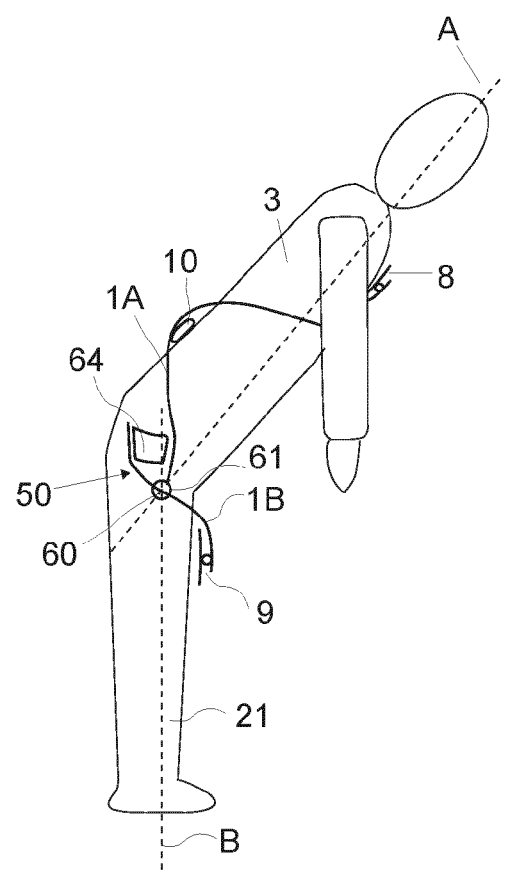
Figure 15A:
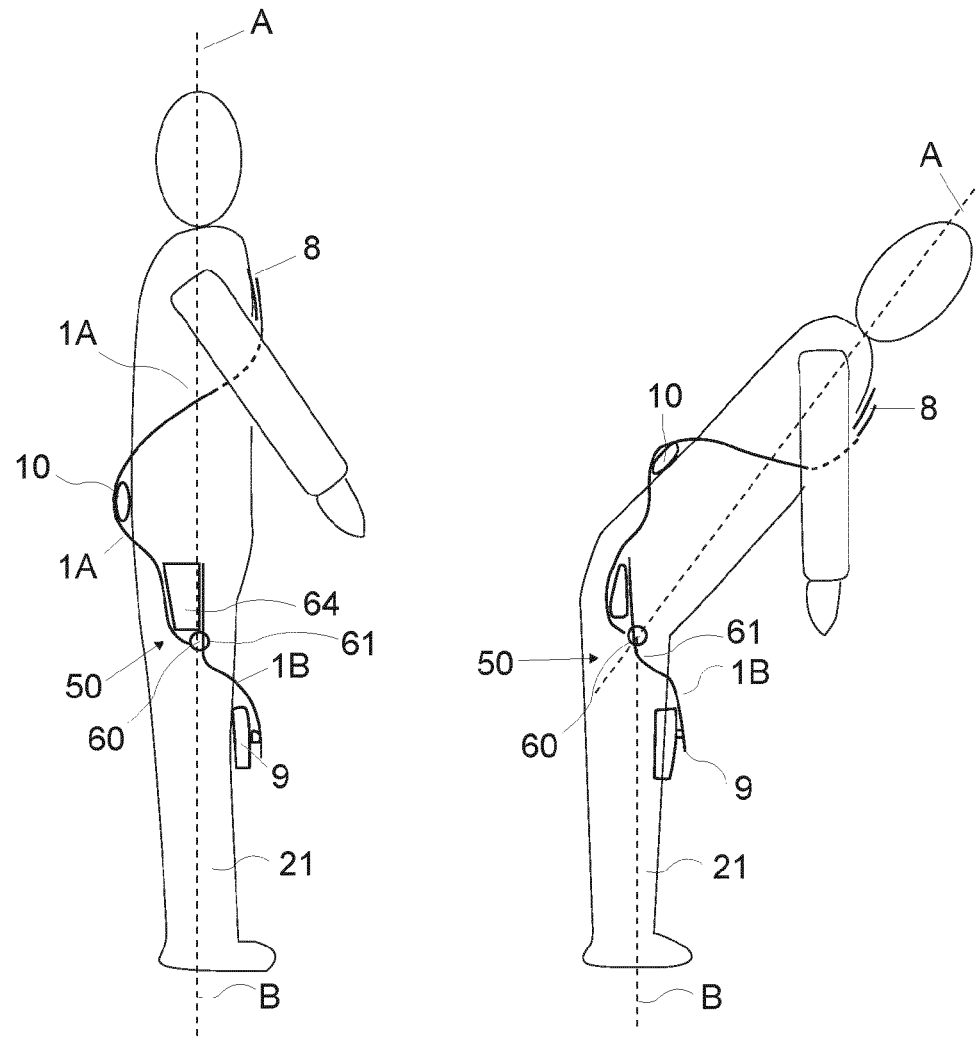
Figure 16A:
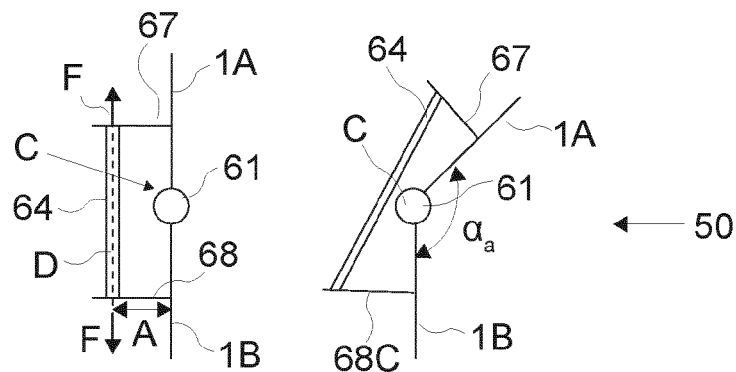
Figure 16B:
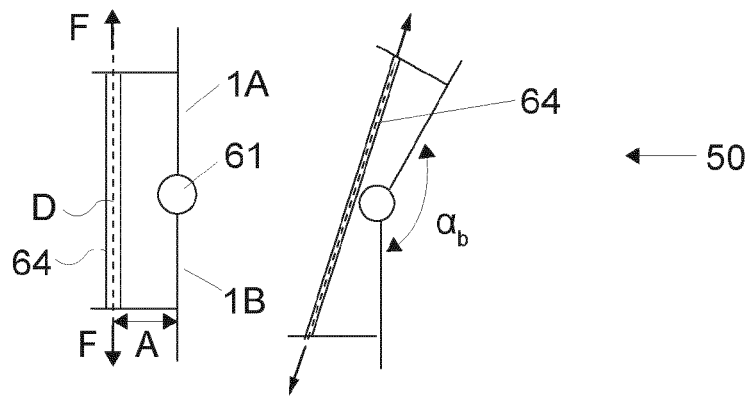
Figure 16C:
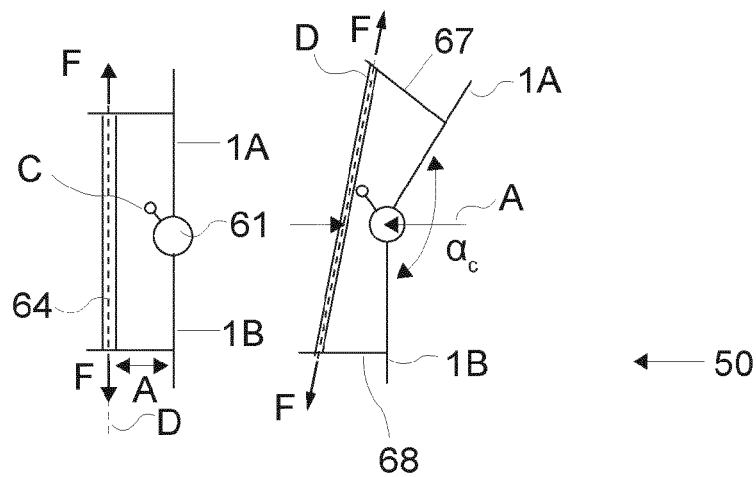
Figure 17:
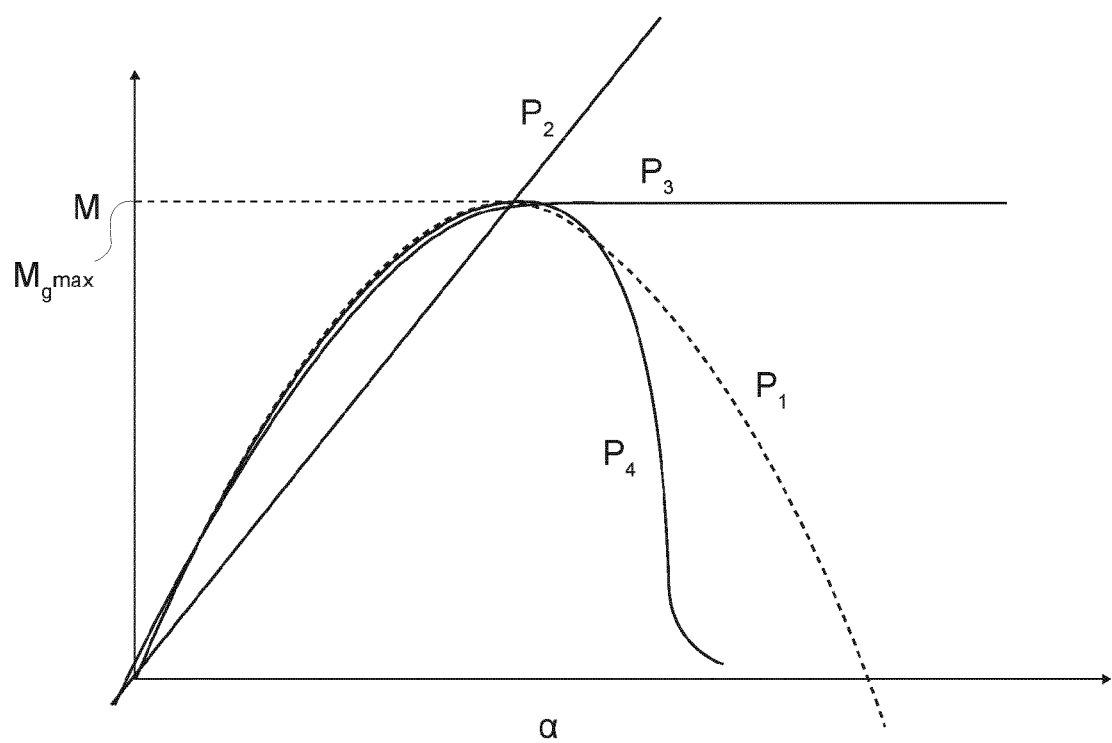
Figure 18:
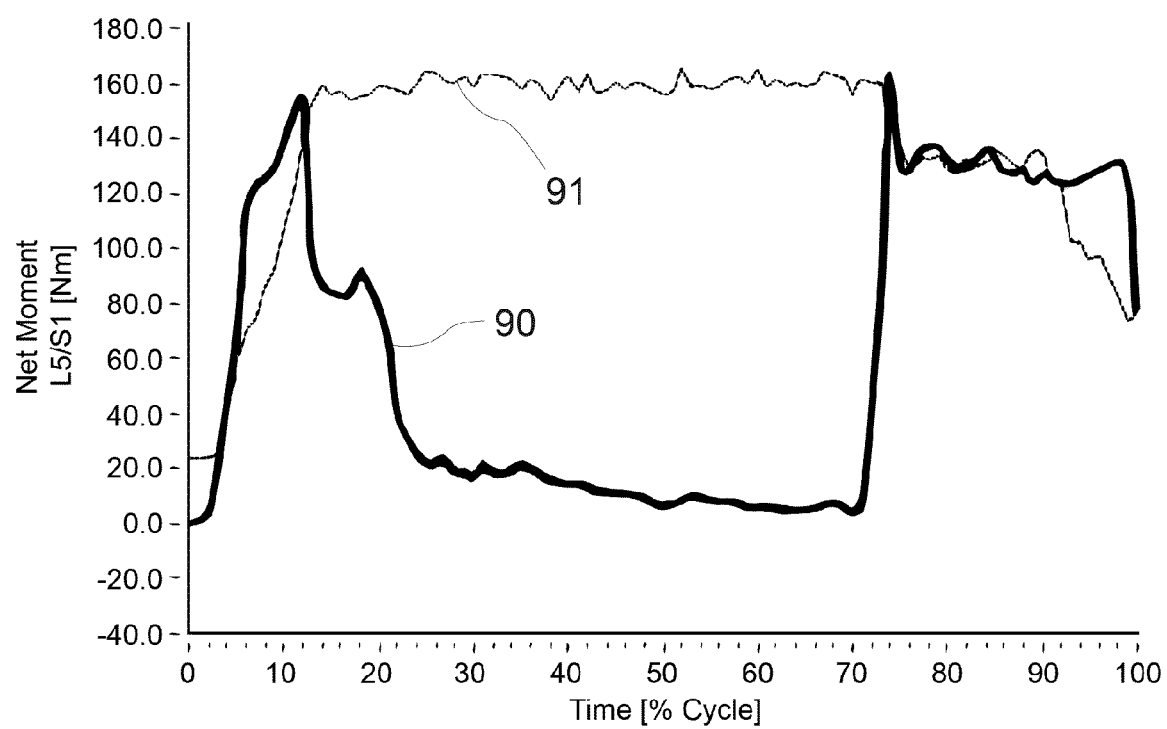
Figure 19:
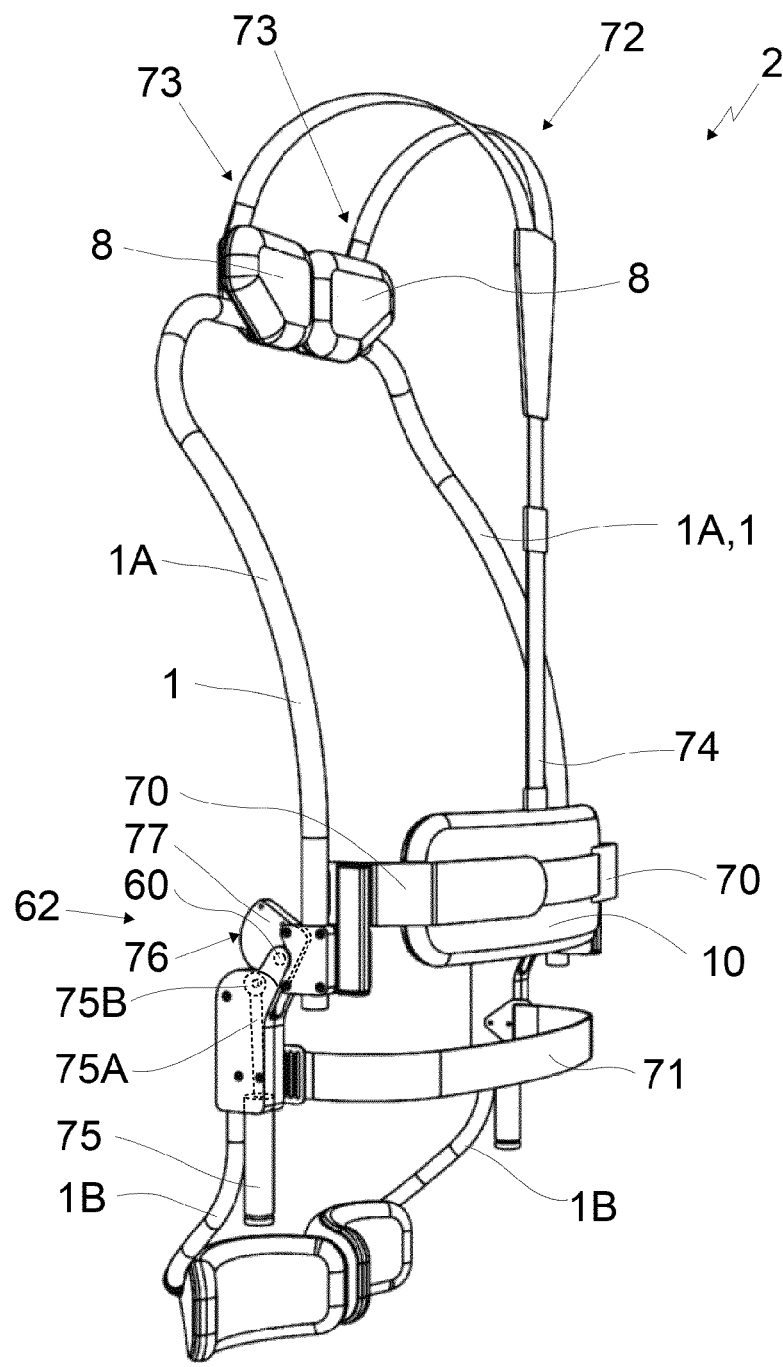
Figure 20:
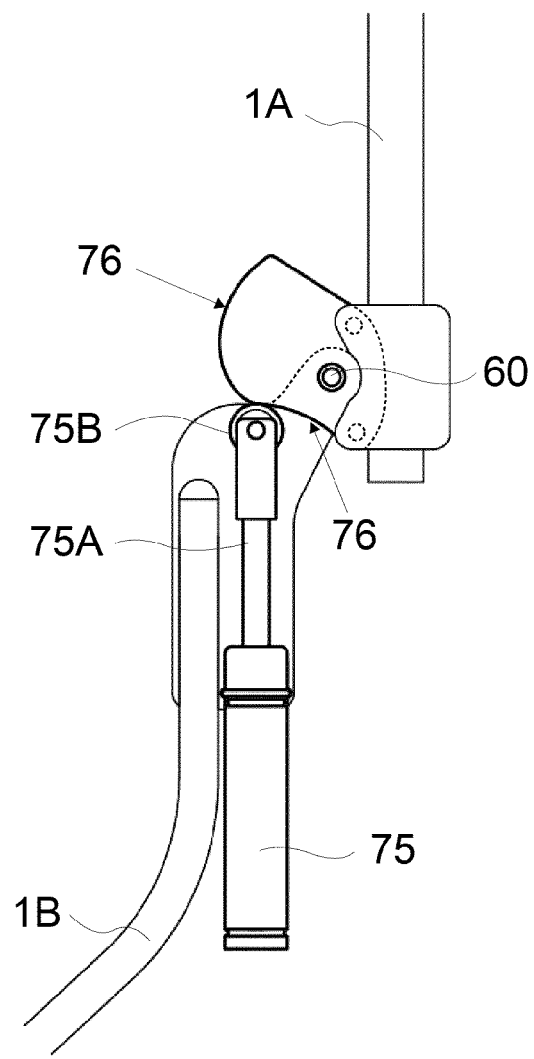

FIGS. 5A and B are views of a person wearing the wearable structure under a piece of clothing, from a side and the front respectively;

FIG. 6 is a schematic view of a human in upright position wearing a support structure comprising two stays;

FIG. 7 is a schematic view of a structure according to the description, comprising two stays, shown in both side view and frontal view;

FIG. 8 is a schematic view of a person wearing a wearable structure, in bent over position showing forces and moments;

FIG. 9 is a schematic diagram of a possible relation between the angle between the upper body and the legs of a person wearing the wearable structure and the force exerted by the structure on the upper portion of said body;

FIG. 10 is a schematic view of some embodiments of supports to be used with a wearable structure, such as but not limited to structures as disclosed in the present disclosure;

FIG. 11 is a schematic view of a support comprising a pivot with resilient means, on a person standing straight;

FIGS. 12A and B are schematic views of the support of FIG. 11, with the person bending over forward over a first angle and a second angle respectively;

FIG. 13 is a schematic view of the support of FIGS. 11 and 12, with the person squatting;

FIG. 14 is a schematic view of an alternative embodiment of a wearable structure of the disclosure, worn by a person standing straight up;

FIG. 15 is a schematic view of the wearable structure of FIG. 14, with the person bending over;

FIG. 15A is a schematic representation of an alternative embodiment of a support structure worn by a person, standing straight up and bending forward;

FIG. 16A-C show different possible layouts, by way of example, schematically, of a pivot construction for a structure of the description;

FIG. 17 is a schematic diagram showing different moment curves for a support, depending on flexibility of the stays and/or pivot of a support, in relation to the bending moment in a rod or torsion spring when bent or twisted;

FIG. 18 is a schematic diagram showing a lower back area moment curve for a person bending over with a structure according to an aspect of the invention and a lower back area moment curve for a person bending over without such structure;

FIG. 19 shows a schematic view of an alternative embodiment of a wearable structure according to an aspect of the present disclosure;

FIG. 20 shows a detail of the structure of FIG. 19; and

Figure 21A:
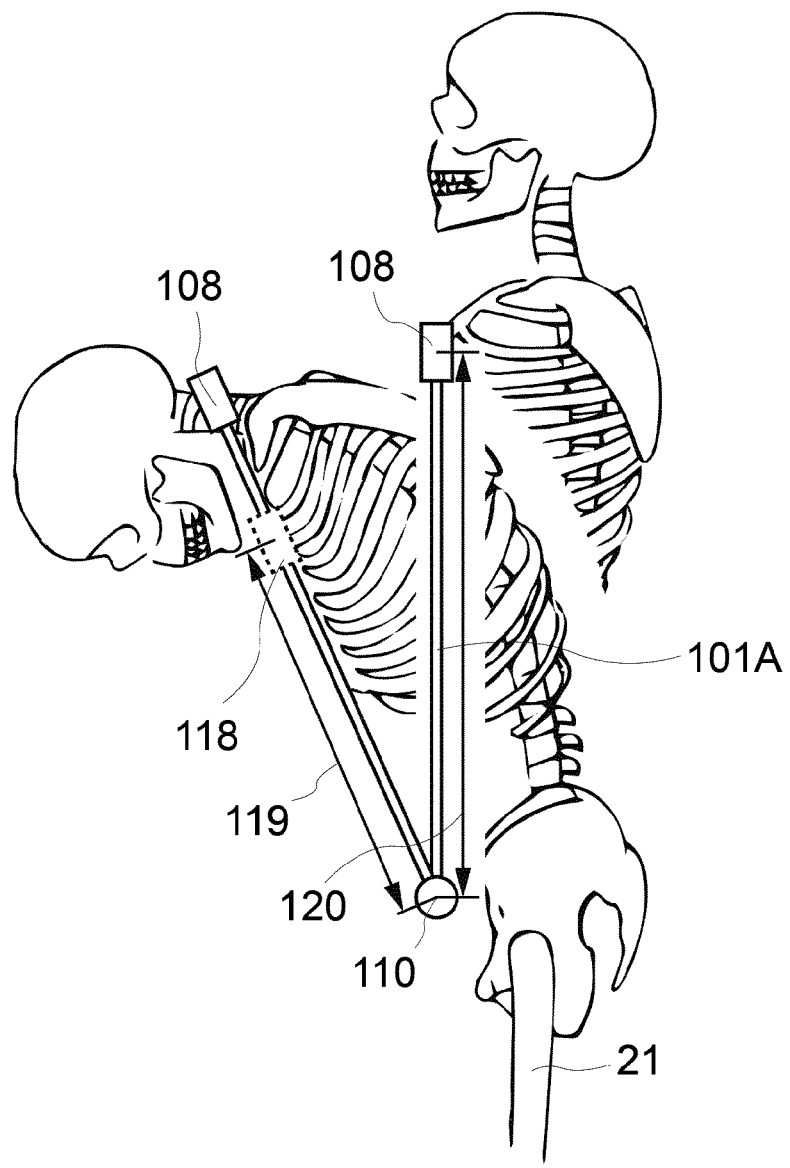
Figure 21B:
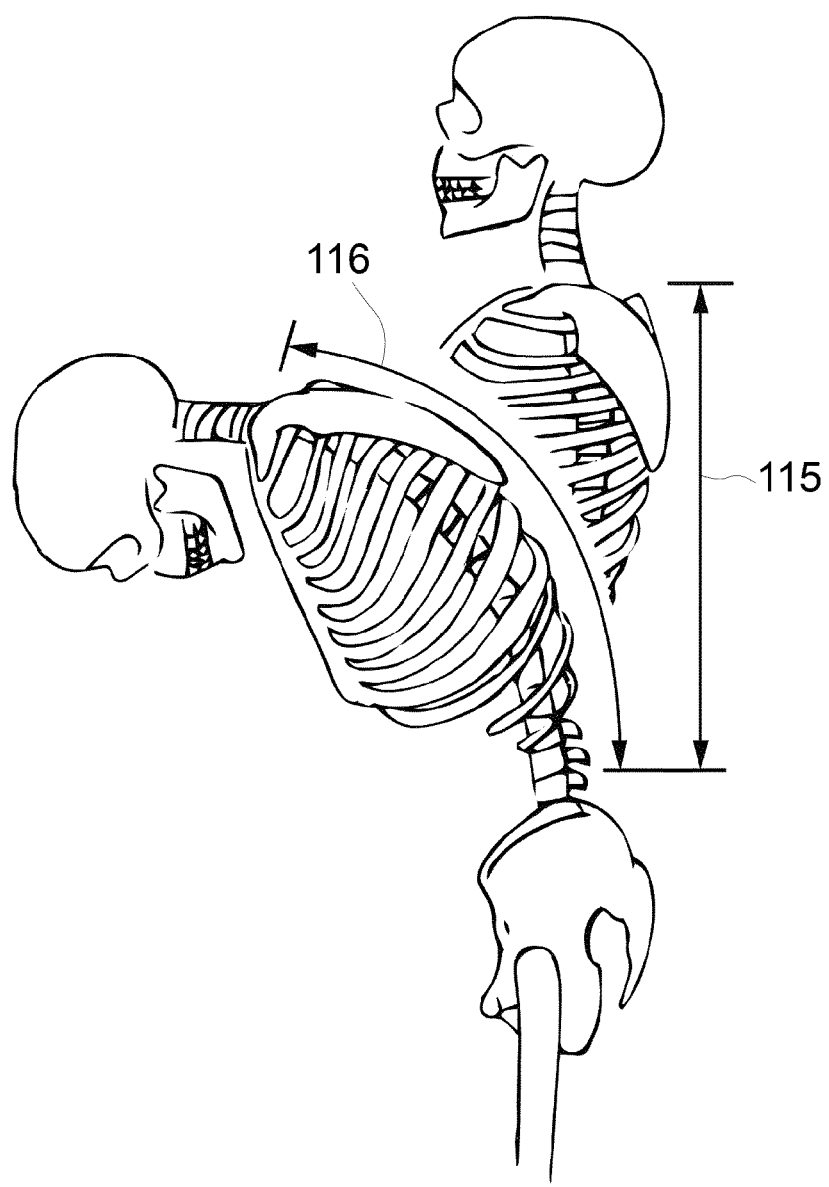
Figure 21C:
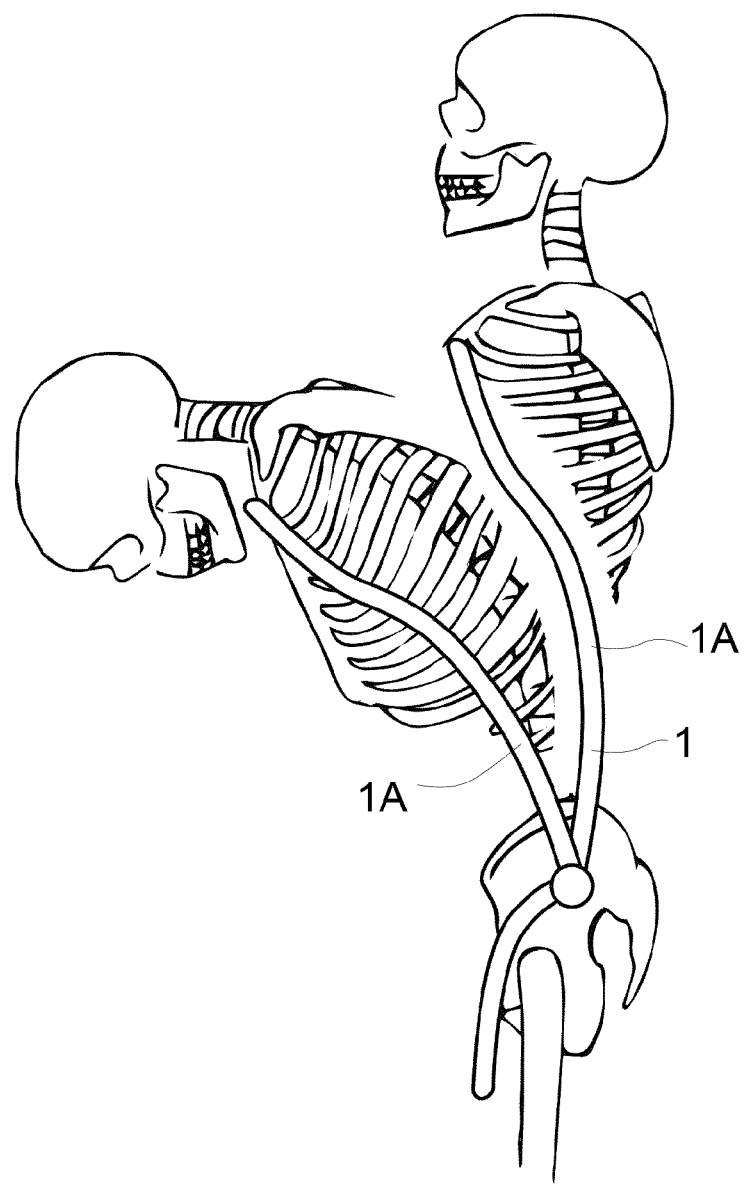

FIGS. 21A-21C shows schematic side views of a skeleton of a user of a wearable structure in both an upright position and a bent position.

In this description and the drawings the same or similar elements have the same or similar reference signs. In this description the invention shall specifically be described with reference to embodiments of a structure, set and method of the disclosure, by way of non limiting examples only.

In this description any masculine reference to humans should be understood as being equally applicable to feminine humans too.

In this disclosure a stay has to be understood as a support element, including but not limited to a strip, which may be bent in one or more positions and directions, and which may carry or include support elements such as, but not limited to, padding, support shells, cushioning or the like. A stay can be made of any suitable material, such as but not limited to plastic, metal, composite materials and the like, or combinations thereof.

In this disclosure an upright position of a body is to be understood as meaning a position in which the trunk or torso of the body is substantially directly vertically above the hips and/or legs. A stretched state has to be understood as substantially a position in which the at least one stay will be in when the stay is not externally loaded by any force, or at least not externally loaded by any force other than a force clamping the stay to the human body when in the upright position. In other words the stretched state can be understood as the state of the stay when for example laying on a table without being engaged or when worn properly by a user, the body of the user being in an upright position or at least having his or her body in a straight, unbent position. When bent the stay will be biased to recover the stretched position as much as possible, thus exerting a force onto the human body of a wearer, back towards the upright position.

In this disclosure supporting can be understood as providing a force sufficient to support part of the weight of the upper body when moved away from the straight, upright body position.

In this disclosure substantially, about and similar wording is to be understood as meaning that any feature with such definition can differ from a given value, for example up to 20%, or up to 15%, such as up to 10% or at least up to 5%. In this description front (anterior), back (posterior), up and down and sides are references to positions and directions and the like, as commonly considered with reference to the sagittal or lateral plane, coronal or frontal plane and axial or transverse plane of a person standing straight up. Up is referred to as in the cranial direction, down in the opposite direction. When using these terms with reference to the structure or parts thereof these are considered with reference to the structure as if it were worn by such person standing up straight, unless specifically shown and/or described differently.

In this disclosure a moment M is to be understood as a biasing moment, i.e. a moment biasing the structure towards a stretched state, especially the or each stay. Such moment M will provide a force acting through the chest support(s) on the chest of a person wearing the structure. In embodiments where there are two stays in the structure and/or one or more pivoting structures, they together provide the moment M.

Figure 1:
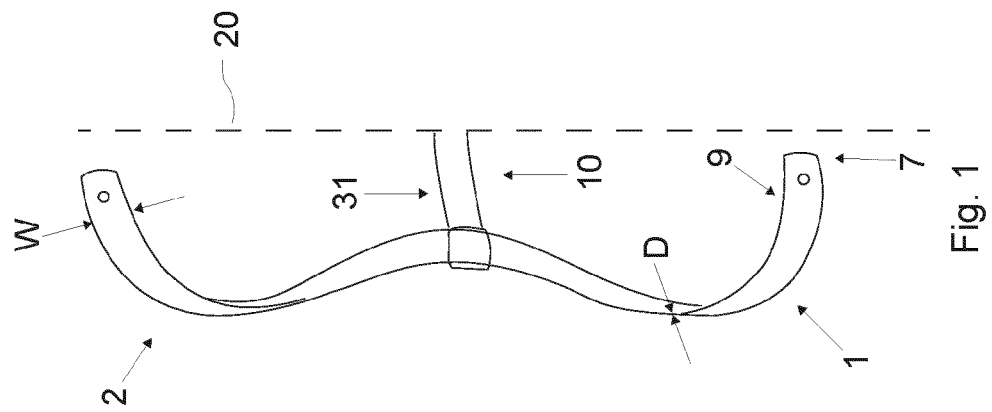
FIG. 1 is a schematic perspective frontal view of a stay.
Figure 2:
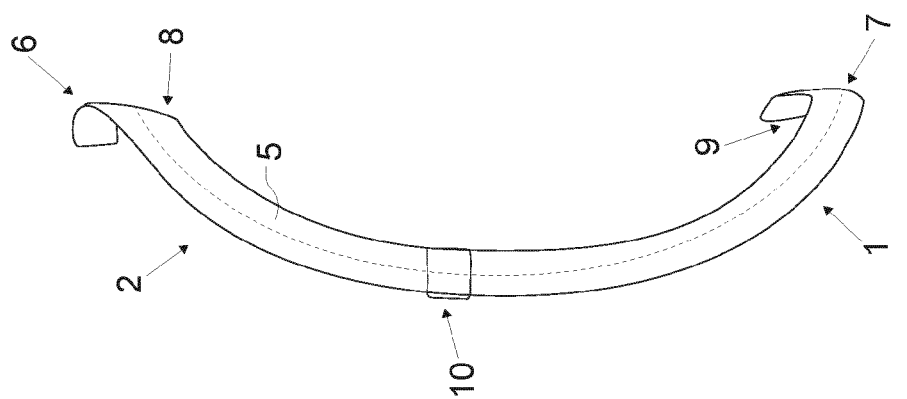
FIG. 2 is a schematic perspective side view of the stay of FIG. 1.

FIGS. 1 and 2 show an embodiment of a stay 1 forming or for forming a wearable structure 2 for supporting an upper part 3 of a human body 4, especially the torso. It should be noted that the structure 2 and parts thereof will be described with reference to a human body of a wearer of the structure 2. The human is obviously not part of the invention as claimed. In the embodiment of FIGS. 1 and 2 the stay 1 is formed by a strip 5, curved in three dimensions, between two opposite ends 6, 7. The first end 6, which can be referred to as upper end 6, forms or can be provided with a first support 8, which may also be referred to as chest support 8, which can be arranged for bearing upon a chest area. In this disclosure chest area can be understood as including but not limited to an area located at and/or near a front side of a thorax, and/or can be understood as including but not limited to an area located at and/or near the sternum or so-called breastbone and/or one or more ribs The second end 7, which can also be referred to as lower end 7, can form or can be provided with a thigh support 9, which can be arranged for bearing upon a thigh area. In this disclosure thigh area can be understood as including but not limited to an area located at and/or near a front side of the upper leg, and/or can be understood as including but not limited to an area located at and/or near the femur. In between the upper and lower ends 6, 7 a third support or lumbar support 10, which can be arranged for bearing upon a lumbar area, can be provided or such lumbar support 10 can be formed by, on and/or in the stay 1. In this disclosure lumbar area can be understood as including but not limited to an area located at and/or near the lower end of the back of a human body, and/or can be understood as including but not limited to an area located at and/or near the lumbar vertebrae and/or the pelvis, wherein the pelvis can be understood as including but not limited to the hip bones or so-called pelvic bones, the sacrum, and/or the coccyx or so-called tailbone. In a relative simple embodiment as shown in FIGS. 1 and 2 the ends 6, 7 form a chest support and thigh support 8, 9, whereas a portion 10 of the stay 1 forms the lumbar support portion. In such embodiments padding can be provided in said support areas, in order to provide comfort when wearing the support structure 2. This padding can extend over part or all of the stay or stays 1.

FIG. 3 shows an alternative embodiment of a stay 1, wherein support elements 8A, 9A and 10A are shown, connected to the stay 1 and forming a chest, thigh and lumbar support 8, 9, 10 respectively. In embodiments the elements 8A, 9A, 10A can be attached directly to the stay, for example in a fixed position. In an alternative, as shown in FIG. 3, the elements 8A, 9A, 10A can be mounted in the stay 1 flexibly, such that their position can shift relative to the stay, especially pivoting, due to forces exerted thereon by the body 4 during use. This can increase the comfort and support from the stay 1 and thus of the structure 2 relative to the body in use. In FIG. 10 some embodiments of such elements 8A, 9A, 10A are shown, by way of example only, which will be discussed further here below. The elements 8A, 9A, 10A can be padded or can be made of a relatively soft padding material in part or entirely, increasing wearing comfort.

In the embodiment of FIG. 3 the stay 1 is shown divided into an upper part 1A and a lower part 1B. The upper part 1A has a lower end 25 and the lower part has an upper end 26, each of said ends 25, 26 being provided with cooperating connecting elements, such as for example openings 27 through which a bolt 28 or such element can be inserted in order to connect the two parts 1A, 1B. By providing a series of such connecting elements in at least one of the parts 1A, 1B, the length of the stay 1 between the ends 6, 7 can be adjusted, for example for fitting the structure to a taller or shorter body 4 and/or different body proportions. In embodiments the connecting elements 27 can be provided such that also the angle $\beta$ between the length direction $Z_1$, $Z_2$ at the lower and upper ends 25, 26 respectively of the upper and lower stay parts 1A, 1B can be adjusted, for example for arranging the structure for a larger or smaller body 4. In the embodiment shown the connecting elements 27 are provided above the lumbar support area. They can however also be provided additionally or alternatively below the lumbar support area. The position of the lumbar support can also be adjustable. Many alternatives for such adjustment means will be directly apparent to the skilled person, such as but not limited to telescopic means, foldable means and the like.

A stay 1 of a structure 2 can be made of any suitable flexible material, such as but not limited to plastic, metal, composite materials such as but not limited to fibre, especially glass, glass fibre and/or carbon fibre filled materials, sandwich materials of such materials or the like, and can have any suitable cross section to provide resilience and flexibility sufficient to provide sufficient support for an upper part 3 of the body 4 which can aid a person wearing the structure 2 when bending over forward and/or sideways, for example during lifting of a load, performing a task bending and/or reaching, for example in a working environment. A stay can for example be made of glass or carbon filled material such as plastic. In a suitable embodiment the stay has a substantially constant cross section perpendicular to a direction between the ends 6, 7 along a surface of the stay. In such embodiment a stay 1 could for example be formed by bending a straight strip of material having a constant width W and thickness D into the desired three dimensional shape, as shown for example in the drawings, or by forming such strip directly in the desired shape, for example in or on a mould. In alternative embodiments the cross section can differ over the length of the stay, for example in width and/or thickness and/or shape of the cross section, in order to optimize for example flexibility and/or rigidity of the stay over its length. Alternatively and/or additionally material properties of the stay can differ over the length of the stay, for the same or similar purpose.

In this description the length direction of a stay 1 is considered to extend between the opposite ends 6, 7, along the stay, a thickness D of the stay is considered in any position the smallest dimension of the stay 1 in that position, measured perpendicular to the length direction in that position and the width of the stay in any position the largest dimension of the stay 1 in that position, measured perpendicular to the length direction in that position.

As can be seen in FIGS. 4-8 a stay 1 can be positioned on a body 4 of a human, such that it partly extends alongside said body, such that the chest support 8 rests against the front side of the chest area 11 of the body 4, the thigh support 9 rests against at least a front side and/or inner side of the thigh 12 of the body and the lumbar support 10 rests against the back of the lumbar portion 13 of the body 4. The stay 1 extends alongside the upper portion 3 of the body 4 below an armpit, leaving the shoulders and shoulder region 14 of the person free, thus not hindering the persons freedom to move his arms and shoulders and preventing undesirable stress and strain in said shoulder region. Surprisingly it has been found that the chest supports 8 as provided by the present disclosure are conceived as more comfortable than supports on the shoulders as used in the prior art.

By arranging the structure such that the thigh support 9 rests at least partly against the inner side of the thigh 12, it may be counteracted that the structure 2 and/or the stay 1, especially a lower stay part thereof, can flip or twist off the upper leg relatively easily.

Additionally or alternatively, the frame of the structure 2 can be arranged to keep the neck portion of the human body substantially free. The stay 1 may extend alongside the upper portion 3 of the body 4 below an armpit, thereby leaving the neck portion, and/or at least the throat, of the person substantially free.

The stay 1 extends alongside the lower sides 15 of the upper part 3 of the body 4, leaving the ventral or stomach area 16 free from the structure 2. This means that the structure does not interfere with or hinder bending of the body in the sagittal and/or coronal plane at the hip or pelvis region 17. The stay 1 curves around said lower sides 15 towards the back of the body at the lumbar or lower back region 18, forming and/or connecting to the lumbar support 10 and then back towards the front of the body 4 again over the side of the hip or pelvis region 17, to the front area of the thigh 12, forming and/or connecting to the thigh support 9. Thus this allows lifting of the leg i.e. bending of the leg at the hip relatively freely.

The stay 1 can be dimensioned and shaped such that for placing the structure 2 onto the body 4 of a person standing upright, the chest support or supports 8 and/or the thigh support or supports 9 have to be pulled forward slightly, relative to the lumbar support or supports, such that when released to the body the chest support or supports and/or the thigh supports 9 and the lumbar support or supports 10 is/are clamped onto the body 4 by elastic force resulting of slight deformation of the stay or stays 1.

In this description a stretched state of a stay 1 is for example shown in FIGS. 1-4, 5B, 6 and 7 and is to be understood as meaning a position of the stay 1 in which it is when not engaged by external deformation forces, other than when applicable resulting from the slight deformation of the stay or stays due to the clamping of the structure 2 onto the body of a person standing upright. In other words, a stretched state or so-called relaxed state of a stay can be understood as the position of the stay 1 when worn on the body 4 being in a relaxed position, such as a body sitting or a body standing upright, as shown in the said figures. In FIGS. 5A and 8 the or each stay 1 is shown in a non-stretched state, which can also be referred to as a bent state, resulting from bending the body 4 in the hip or pelvic region 17, thus reducing the angle α between the legs 21, especially the thighs 12 and the upper body 3.

The or each stay can be bent and/or twisted in order to be brought and/or held in the bent state, for example when a person wearing the structure bends his body or squats. For example, a portion of the stay 1 near a side of the body 4 can have a cross section with the width direction W substantially in a plane parallel to the sagittal plane. This section therefore has the largest area moment of inertia, i.e. the largest resistance against bending in said plane. Upon bending the body the stay(s) will be bent and twisted, such that said cross section is rotated relative to said plane and/or is twisted elastically, reducing the resistance against bending in that plane, such that further bending of the body may become easier. This reduction may occur after an initial bending over an initial angle $α_1$ of the body 4.

As can be seen in e.g. FIG. 5-8 a structure 2 can comprise two stays 1, which may be mirror symmetrical relative to the intermediate sagittal plane 20. This means that the structure 2 will provide substantially symmetrical support from both the left and the right hand side of the body, seen from the front or back, when bending in the sagittal plane. A structure 2 will allow twisting of the stay or stays 1 relatively easily, i.e. without high torque in the or each stay, such that the person can rotate his upper body part 3 relatively freely, without experiencing an undesirable high force in the opposite direction. Moreover the structure 2 allows bending of the upper body sideways, i.e. in the coronal plane 19, experiencing a counter pressure from the or each stay 1 due to bending thereof.

In FIG. 7 a structure 2 is shown, comprising two stays 1, which are connected to each other in the lumbar region, near the lumbar supports, by a connection 30 and in the chest area near the chest supports 8 by a connection 31. In other embodiments only one such connection 30, 31 can be provided, or more than said two and/or in different positions. The or each connection can be releasable, for example by using releasable connecting elements such as clips, straps, Velcro® type connectors or the like. There can be at least one such connection, which can advantageously be provided in the lumbar area, such that the chest supports 8 and thigh supports 9 can be pushed or pulled further apart to fit the structure as if fitting a coat to the body 4. The structure 2 can be fitted from behind and closed in front by placing the chest supports 8 on the chest and the thigh supports 9 on the thighs, thereby pulling the lumbar support or supports against the lower back of the body 4. If applicable then the connection 31 can be closed, ensuring a proper fit is maintained even further. In FIG. 6 in stead of at least the connection 30 a strap 32, e.g. a belly band, is provided around the waist of the body, aiding in holding the structure 2 in proper position during use. For example, in such a proper position, the structure 2 may be worn relatively close to the human body, which can make the structure feel more comfortable during walking and/or prolonged use. The strap 32 can be additional to or alternative to the connections 30, 31.

In embodiments the structure can comprise two stays, integrated into a singular structure by an integrated connection 31 between the stays, especially close to or in the lumbar region. A connection between the stays, especially in the back such as at the lumbar region, preferably is sufficiently strong to keep the stays 1 together during use, but sufficiently flexible to allow relative movement, for example for allowing walking and rotating of the upper body 3 without significant hindering.

The or each stay 1 can be bent such that in an area 22 between the chest support 8 and the lumbar support 10 and/or in an area 23 between the lumbar support 10 and the thigh support 9 the width direction W of the stay extends substantially parallel to the sagittal plane 20, whereas between said area 22 and the chest support 8 and/or between said area 22 and the lumbar support 10 and/or between said area 23 and the thigh support 9 and/or between said area 23 and the lumbar support 10 the stay may be curved such that the said width direction W is rotated towards a position substantially parallel to the coronal of frontal plane. Thus bending of the stay 1 in said area or areas 22 and/or 23 in a plane substantially parallel to the sagittal plane 20 will be more difficult than in a direction substantially perpendicular to it, whereas in or near the lumbar area this will be the reverse: there bending of the stay may be easier in a plane substantially parallel to the sagittal plane than in a plane substantially perpendicular to it. The resistance against bending and thus the flexibility of the stay 1 can differ locally along its length direction, by e.g. changing the cross section locally and/or changing the position of the cross section relative to the sagittal and coronal plane. Thus the flexibility of the or each stay 1 can be optimized.

FIGS. 5A and B and 6 show the wearable support structure 2, for example according to FIG. 7, worn by a person on the body 4. In FIG. 5 the wearable support structure 2 is shown (to be) worn below a piece of clothing 29, here shown as a coat, especially a lab coat. In FIG. 6 the wearable support structure 2 is shown worn over the clothing 29.

In embodiments the structure 2 can be connected to or integrated with a piece of clothing 29. In the embodiment of FIGS. 5A and B the structure 2 can be connected to or integrated with the piece of clothing 29. In this embodiment at least one of the stays 1 extends through a sleeve provided in the back of the clothing 29, for example such that the lumbar support is encased within said sleeve. This prevents that the clothing 29 and the structure get easily separated inadvertently. Alternatively or additionally the piece of clothing can be attached to the structure, especially the stay or stays 1 in other positions, for example near the chest supports 8 and/or near the thigh supports 9, for example by hooks, straps, Velcro, clips, buttons, zippers or the like. Thus by putting on the piece of clothing 29 automatically also the structure 2 will be placed on the body 4. Preferably connections between the structure 2 and the piece of clothing are releasable, such that they can be separated relatively easily in order to for example be cleaned, stored, exchanged and/or used by other users, or in order to allow the piece of clothing to be worn without the structure 2 too. When worn with and, especially when integrated with or connected to a piece of clothing, two separate stays 1 could be used for forming the structure, as long as they are then held in an appropriate relationship with respect to each other by said clothing 29.

In FIG. 7 at least one sensor 33, more specifically two sensors are shown, one on each stay 1. Sensors 33 can be used for registering for example forces exerted on and/or by the structure 2 and/or on the body, movement patterns, angles and the like. Known type sensors such as strain gauges, acceleration sensors, inclinators, proximity sensors and the like, or combinations of such known sensors can be used. The sensors can be connected to control, including a data gathering system (not shown) in a known manner, via a wire or wireless. The control can be stationary or portable.

In FIG. 8 a person is shown, wearing a structure 2 according to the disclosure, bending over forward, in this figure substantially in the sagittal plane, reducing the angle α between the thigh 12 and the upper body or torso 3. For simplicity sake in FIG. 8 a general direction A of the torso 3 is shown extending perpendicular to an imaginary axis 34 of rotation through the hips and through the head 35 of the person, central to the torso 3, and a general direction B of the legs, especially the thighs 12, central between the legs, perpendicular to the said axis 34 and crossing the axis A. In upright position of the body the axis A and B coincide and the angle α will be 180 degrees. As can be seen in FIG. 8 the centre of gravity Z of the upper body or torso 3, including arms and head, will be brought forward over a distance X, said distance increasing within a decreasing angle between 180 and 90 degrees. Thus the moment $M_g$ resulting from said bending around the axis 34 will also increase accordingly, due to the gravity force $F_g$ and the increasing distance X. Since the stay or stays 1 are flexible and are in fact deformed, especially bent and/or twisted, they will provide a counter force $F_s$ which will lead to a moment $M_s$ contrary to the moment resulting from the gravity force $F_g$. $M_s$ will be equal to Fs*P, wherein P is the distance between the axis 34 and the chest support which will be substantially constant. The force $F_s$ resulting from the deformation such as bending and/or twisting of the stay or combined stays 1 can be such that the moment $M_s$ around the axis 34 compensates at least in part and preferably to a high degree, for example at least 50%, more preferably at least about 75% or substantially entirely for the moment $M_g$ around the axis 34 resulting by the gravity on the torso 3. Thus the upper body 3 or torso of the body 4 will be supported by the structure 2 when bending the body 4. FIG. 9 shows schematically, by way of example, a relationship between the angle α and the moment $M_s$ resulting from said bending.

Figure 5B:
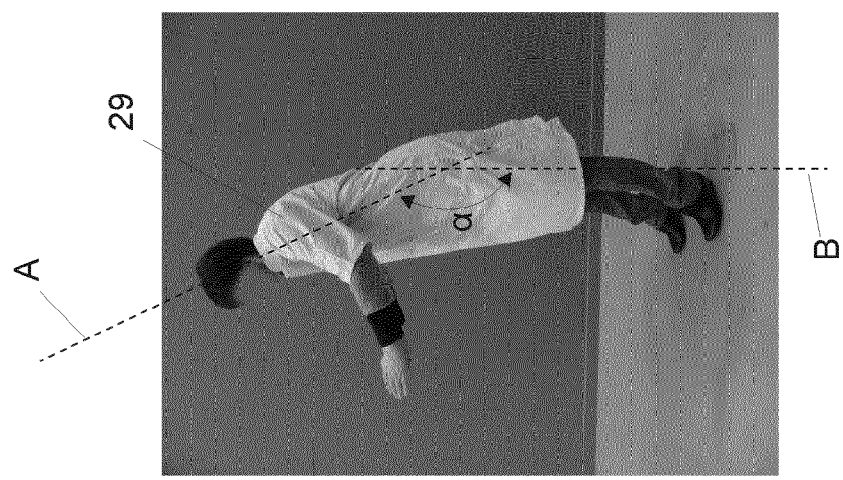

As can clearly be seen in FIG. 5B the entire stomach area of the body can be free. Similarly the entire shoulder area can be free from the structure 2. Thus a person wearing the wearable support structure experiences a minimum of or possibly no interference of his movements by the structure 2 while wearing it. The structure can be relatively light and comfortable, can be easy in use and maintenance and can in embodiments be fitted to different body sizes and shapes.

FIG. 10 schematically three embodiments of a support element T are shown, which can be used as chest, thigh and/or lumbar support 8, 9, 10. Here they shall be discussed with reference to a chest support 8, by way of example only.

In each of these embodiments the elements comprises a carrier 36 which may have any suitable shape and dimensions, for example flat or curved, and which may be relatively stiff. Such carrier can for example be made of plastic, metal and/or wood or any other suitable material. On one side of the carrier 36, in use facing the body 4, a padding 37 is provided, for example made of foam, elastomer, natural materials such as fibres, artificial fibres or the like, which padding may comprise a cover 38, such as but not limited to cloth, fabric, plastic, leather the like, for protecting the padding, providing for comfort and moreover cleanability. The padding preferably is relatively soft in order to provide for adaptability to the relevant body area and positioning of the padding 37, but sufficiently rigid to be able to transfer the forces acting on it through the body to the structure or vice versa. At an opposite side a connecting means 39 can be provided, connected to the carrier 36 and to the relevant stay 1. The connecting means 39 can be relatively rigid, fixing the padding in a single position, but preferably the connecting means provides for flexibility in order that the position of the support element T can be changed. In the embodiment shown at the upper left hand corner in FIG. 10 the connecting means comprise a flexible block 43, for example an elastomer or rubber block or a layered structure of more and less flexible and/or compressible material layers, adhered to the carrier 36 and the stay 1 or otherwise attached to them. In the embodiment at the right hand upper corner the element 8A is connected to the stay 1 by a rubber or elastomeric, flexible element 40, mounted between the carrier 36 and a pin 41, wherein the pin is connected to the stay 1, for example screwed into the stay or welded to it or otherwise attached. In this embodiment the element 40 provides for flexibility. In the embodiment at the lower side of FIG. 10 the element 8 is connected to the stay by a ball joint or similar pivot or hinge construction 42. In all of these and similar connections the element 8A and/or 9A and/or 10A is connected flexibly to the relevant stay 1, such that its position relative to the stay and/or body can easily be adapted especially will be automatically be brought into a desirable position when placing the structure 2 on the body 4. Thus the comfort of the structure, when worn, can even further be increased. Preferably the element 8A, 9A, 10A is biased into a neutral position, more preferably by the block 43 or element 40.

FIG. 11-13 disclose a support according to the present disclosure in an embodiment in which an upper part 1A of the stay 1 and a lower part 1B of the stay 1 are connected pivotally by a pivot provision 50, which preferably has a fixed pivot axis 60 during use. Fixed should in this respect be understood as in a fixed position relative to the lower end 25 of the upper stay part 1A and the upper end 26 of the lower stay part 1B. The pivot axis 60 preferably extends substantially perpendicular to the sagittal plane 20 and parallel to the transverse plane when a person wearing the structure is standing up straight. In the embodiment shown in FIG. 11-13 the support structure 2 comprises again two stays 1, one for extending alongside each of the opposite sides 15 of the body as discussed here above, wherein each stay 1 comprises a pivot 61 between the upper and lower stay part 1A, 1B next to the hip of the person wearing the structure 2, such that the pivot axis 60 extends substantially through the virtual axis 34 of bending of the upper body 3 relative to the legs 21 at the hip/pelvic region. In embodiments the upper and lower stay parts 1A, 1B can be as described here above, for example having flexibility in at least one direction of bending higher than in a direction perpendicular to that direction. In other embodiments the upper and lower stay parts 1A, 1B may be designed differently, for example relatively stiff, such that when a person wearing the structure is bending over the movement of the upper part 1A relative to the lower part 1B of the stay is mainly obtained by pivoting at the pivot axis 60.

The structure 2 in embodiments comprising a pivot provision 50 between upper and lower stay parts 1A, 1B of a stay 1 forms, as discussed before with respect to the previously discussed embodiments, a wearable support structure 2 for at least partly relieving a human body during leaning forward or bending over. The structure can comprise a frame having at least one upper stay part 1A attachable to a torso of a human body and at least one lower stay part 1B attachable to un an upper leg of a human body, wherein the upper stay part and the lower stay part are pivotably connected to each other. The structure 2 can be arranged such that the upper stay part 1A and the lower stay parts 1B can substantially pivot with respect to each other at or near an axis of rotation of a hip joint of a human body bending over. Upper and lower stay parts 1A, 1B could also be referred to as stays 1A and 1B. The structure further comprises at least one biasing means 62 and is arranged such that during use the upper and lower stay parts 1A, 1B are biased towards a stretched state corresponding with an upright position of a human body, as discussed before.

The lower end 25 of the upper stay part 1A and the upper end 26 of the lower stay part 1B can be provided with cooperating pivoting means 63A, 63B forming a pivot or hinge 61, during use positioned aside a human hip, especially at or near the axis of rotation of a hip joint of a human body bending over. The structure 2, especially the stays 1 are again dimensioned and shaped to fit on the human body, having a chest support 8, leg support 9 and lumbar support 10 as discussed before. Preferably the upper and lower stay parts 1A, 1B are dimensioned such that when the structure is fit onto a human body the stays, especially the supports 8, 9 and 10 are clamped onto the relevant parts of the body for self supporting the structure 2 on the body, preferably without the necessity of further attachment means, as discussed with respect to the previous embodiments.

As discussed, the upper and/or lower stay parts 1A, 1B can be flexible, for example as discussed with respect to the previous embodiments, such that upon bending by a person wearing the structure 2, both the stay parts 1A, 1B can pivot around said axis 60 and can bend elastically, for example for providing a further support force or for accommodating slight changes in the relative positions of the different supports due to body movements, and or to allow for for example bending sideways and/or rotations of the upper body relative to the legs c.q. pelvis, rotation of a leg etc. It should be noted that a structure 2 according to the disclosure allows the legs of a person wearing the structure 2 to be moved independently of each other, accommodating easy walking, climbing and the like, due to the individual stays 1 and stay parts 1A, 1B.

The pivoting provision 50 preferably comprises, as shown for example in FIG. 11-13, a resilient element 64 or elements 64, mounted between the upper and lower stay parts 1A, 1B, such that upon pivoting of the upper part 1A relative to the lower part 1B around the pivot axis 60 the resilient element provides for a moment around the pivot axis 60 countering said pivoting. The resilient element 64 can for example be a flexible, resilient plastic or rubber element or a spring or a series of springs or a combination thereof. Preferably the or each resilient element 64 is placed and attached to the stay 1 such that at least one and preferably both ends 65, 66 of the resilient element 64 are connected to the relevant stay parts 1A, 1B respectively spaced apart from the pivot axis 60, more specifically spaced apart from the relevant pivot 61. The resilient element 64 can have a direction D of force F extending between two opposite ends 65, 66 connected to the stay parts 1A, 1B respectively which, when a person wearing the structure is standing up straight, lies spaced apart from the pivot axis 60 over a distance $A_0$, which is in this embodiment during use the maximum distance or arm A. This means that when pivoting the upper part 1A relative to the lower part 1B away from the straight position as shown in FIG. 11 towards a bending position, as shown in FIG. 12A, the resilient element 64 will be extended and/or twisted, increasing the force acting on the parts 1A, B and thus increasing the moment M provided by the resilient element around the pivot axis 60. Thus the moment M can increase with a decrease of the angle $\alpha$, that is when bending over further in at least the sagittal plane, at least over a specific trajectory between the angle $\alpha_0$ and $\alpha_1$, as will be discussed further.

In each of the FIG. 11-13 in a circle schematically a pivot area with a resilient element 64 is shown, relative to the pivot axis 61, showing the lower end 25 of the upper part 1A and the upper end 26 of the lower part 1B of the stay 1, and the pivot 61. Each of the lower end 25 and upper end 26 in this embodiment is schematically shown as comprising a bracket 67, 68 extending away from the relevant part 1A, 1B and providing for an attachment for the opposite ends 65, 66 of the resilient element 64. The brackets preferably are provided such that the resilient elements extends in a plane substantially parallel to the sagittal plane of the person when wearing the structure 2, standing straight up or bending in the sagittal plane. The brackets can extend substantially parallel to each other when the structure 2 is in the stretched position and/or worn by a person standing up straight.

In embodiments the resilient element 64 may have linear properties. In embodiments it can have non-linear properties, especially non linear elastic properties, which should be understood as meaning that the elastic properties are not linear with an extension and/or twisting of the element 64. This can e.g. be understood as a system in which an elasticity coefficient does not vary linearly with space parameters, such as elongation or twisting angle and/or a system in which the Young's modulus of the resilient element 64 is not constant. For example, a nonlinear spring has a nonlinear relationship between force and displacement. A graph showing force vs. displacement for a nonlinear spring will be more complicated than a straight line, with a changing slope.

As can be seen in comparison of FIGS. 11 and 12, when bending over from the standing up straight position as shown in FIG. 11, i.e. in reducing the angle $\alpha$, the minimal distance A between the pivot axis 60 and the direction D of the force (force and arm perpendicular to each other) is reduced to about zero in the position of an angle $\alpha_1$ as shown in FIG. 12A. If from this position the body is bent further, even further reducing the angle $\alpha$ past $\alpha_1$, in this embodiment the resilient element 64 will be forced against a stop C, such as the pivot 61 such that it cannot pass said stop C, such as the pivot 61 or the pivot axis 60. To that end for example also or alternatively a pin can be provided extending from or forming part of the pivot 61, forming the stop C against which the resilient element 64 will abut at about the angle $\alpha_1$. When bending further the resilient element 64 will be bent in the plane parallel to the sagittal plane while the ends 65, 66 are moved with the point of attachment on the brackets 67, 68. In an embodiment in which the resilient element 64 in the position of angle $\alpha_1$ lies virtually against the pivot axis 61 and cannot pass it, the resilient element 64 will have it's maximum length L, measured along a heart line of the element 63 between opposite ends 65, 66.

Upon further bending, i.e. reducing the angle $\alpha$ further, the length of the resilient element 64 will not alter significantly, since the triangles defined by the stop C, such as for example the pivot axis 60, first or second end 64, 65 of the resilient element 64 and the connection between the stay parts 1A, 1B and the respective brackets 67, 68 will not alter substantially anymore. By changing the position C in which the resilient element 64 abuts the pivot provision 50 such that it is stopped from moving further, in a direction towards or passed the pivot axis, the length of the resilient element can be allowed to change slightly upon further bending passed the angle $\alpha_1$, as for example shown in FIG. 16 A-C, by way of example only.

As shown in e.g. FIG. 13 a person wearing the structure 2 can easily squat, without excessive forces, due to the limited moment M in such position.

In embodiments where the length of the resilient element 64 does not change when bending further passed the angle $\alpha_1$, i.e. reducing the angle $\alpha$ further, the arm A for the force F of the resilient element 64 will be substantially zero. If the resilient element 64 substantially only provides a change in force due to a longitudinal extension, such as in a linear or non linear helical spring or an elastomeric or rubber element having a very low bending resistance, the resilient element 64 will then not add to the moment M in either direction. By moving the stop C relative to the pivot axis 60, such that the resilient element 64 does not reach a position crossing the pivot axis 60, upon further bending the resilient element 64 will elongate slightly further, whereas the effective length of the arm A will be small but more than zero, this will lead to a moment M resulting from the resilient element, countering the moment Mg resulting from the mass of the upper body and any load carried.

In embodiments in which a resilient element is used having a relatively high resistance against bending, such as a torsion spring element or an elastomeric or rubber element with relatively large cross section perpendicular to a longitudinal direction between ends 65, 66 and/or made of a material with a relatively high modulus of elasticity, bending of the resilient element will lead to an increasing moment biasing the stay(s) towards the stretched position. This will also be true when the element 64 abuts the stop C and is bent even further. Thus in such embodiment after reaching the angle $\alpha_1$ when the body bends further the resilient element will still provide for a moment biasing the structure back to the stretched state.

The moment M resulting from the force F of the resilient element will at any given angle $\alpha$ be the product of $F_\alpha$ and $A_\alpha$. By choosing the resilient properties of the or each resilient element 64 and the lay out of the pivot provision 50, especially the positioning of the ends 65, 66 of the resilient element or elements 64, the moment/angle curve can be chosen, depending on e.g. the desired compensation of the weight of the upper body of the person wearing the structure at any given angle $\alpha$. Preferably the position of the ends 65, 66 of the resilient element 64 is adjustable relative to the pivot axis 60 and/or the position of the stop C is adjustable relative to the pivot axis 60 and/or relative to the ends 65, 66 of the resilient element 64.

In a stretched position of the stay cq structure and/or in a position when worn by a person standing up straight a longitudinal direction L of said resilient element 64, such as a spring element 64, can be substantially transverse to the axis of rotation of a hip joint of the human body, especially when bending over. At least in a stretched state of the structure corresponding with an upright position of the human body, the longitudinal axis of said resilient element 64 can be spaced away from said pivoting axis 60, especially spaced away over at least 15 mm, preferably at least 25 mm, more preferably at least 35 mm, such as at least 40, 50 or 60 mm, especially at least 70, 80, 100 or 120 mm. Preferably the resilient element is positioned at the rear of the pivot axis. Alternatively it can be positioned at another place, such as for instance substantially above, below and/or in front of the pivot axis 60. Preferably the resilient element is an element to be elongated, such as a spring or elastomeric or rubber element. The longitudinal direction of the resilient element can extend in any direction, for example substantially vertically or substantially horizontally when the person wearing the structure 2 is standing up straight.

The resilient element can be a non linear element such as a spring, especially a spring element exerting a certain force F when elongated over a first distance X and exerting a force smaller than twice the force F when elongated over a second distance being twice as large as the first distance X. Obviously any choice of such linear and/or non linear element 64 can be made depending on the requirements to be met.

In embodiments of the present disclosure the stop C can be positioned relative to the pivot axis 60 and the ends 65, 66 of the resilient element 64 such that the angle $\alpha_1$ is between 90 and 180 degrees, for example between 90 and 160 degrees, such as for example between 90 and 150 degrees. In embodiments the lay out of the pivot provisions 50, such as the position of the attachment of the resilient element 64 to the brackets 67, 68 and/or the position of the stop C can be adjustable, such that the moment curve can be adjusted, especially tailored on for example a user, load expected to be borne by the user and the like.

FIGS. 14 and 15 show an alternative embodiment, in which between the upper and lower stay part 1A, 1B a compressible resilient element 64 is provided. Upon bending of the person wearing the structure 2 the element 64 is at least partly elongated, providing a biasing force F back towards the straight or stretched position. In this embodiment at least the upper stay part 1A and preferably both parts 1A, 1B are relatively flexible, such as for example discussed with reference to the embodiments according to FIG. 1-10, such that part of the bending of the body is allowed by and supported by elastic deformation of the stays 1 or stay parts 1A, 1B, and part by the resilient element or elements 64. Again such resilient element can be chosen with a non linear characteristic, such that for example up to about an angle $\alpha_1$ as discussed with reference to FIG. 11-13 a biasing moment is exerted on the upper body part towards the upright or stretched position, which may for example increase slightly or substantially proportional with the increasing moment resulting from the upper body weight, and upon further bending may be reduced or increase less, in order to allow easy further bending, squatting, walking and such actions and movements of a person while wearing the structure 2.

In FIG. 15A a further alternative embodiment is shown, e.g. similar to that of FIGS. 14 and 15, in which in stead of a resilient element 64 which is elongated a resilient element 64 is used which is compressed. Upon reaching a maximum moment M the further bending may occur in deformation of the or each stay, which can lead to a reduced moment and thus reduced forces countering further bending or squatting. Again such resilient element can be linear or non-linear in behaviour.

By combining flexible stay parts 1A and/or 1B with a pivot axis, the ergonomic compliance and comfort of the structure can be even further increased. The structure, especially the stays will be allowed to even better follow and support movement of the body and parts thereof, such as support for the upper body while bending and at the same time allowing arm, leg and head movements substantially without hindrance.

In FIGS. 16 A and B two different lay outs of a pivot arrangement 50 are shown, in which the resilient element 64 is positioned between the brackets, with the ends 65, 66 spaced differently with respect to the pivot 61. In FIG. 16A the ends 65, 66 are spaced such relative to the pivot 61 that the resilient element 64 abuts the stop C, here shown as the pivot 61, at an angle $\alpha_a$ which is smaller than the corresponding angle $\alpha_b$ in the embodiment of FIG. 16B. In these embodiments the moment M exerted by the resilient element 64 will be reduced sharply or even brought to zero once the resilient element 64 abuts the pivot 61 forming the stop C. In FIG. 16C a similar pivot arrangement is shown, in which however the stop C is spaced apart from the pivot 61. This means that when the resilient element abuts the stop C, at an angle $\alpha_c$, which can be chosen by positioning of the ends 65, 66 relative to the pivot 61 and the stop C, the working line of the force F resulting from elongation of the resilient element will still be spaced apart from the pivot. Thus rotating the upper stay part 1A relative to the lower stay part 1B further will result in a further elongation of the resilient element 64 and moreover will still provide for a biasing moment M towards the stretched position.

FIG. 17 shows a graph showing schematically:
1. A curve P1 showing the moment M exerted by the weight of the upper body relative to the axis of rotation of the hips when bending forward, from a person standing straight up passed a position in which the upper body is substantially horizontal and thus the moment is the largest, to a position in which the person has completely bent over, having his face against his legs. This line is schematically represented as substantially sinusoidal;
2. A curve P2 showing the linear increase of the bending moment of a torsion spring or rod, when bent over an increasing angle;
3. A curve P3 representing a moment M diagram in which in a first trajectory the moment M rises with the angle $\alpha$ substantially identically to the substantially sinusoidal curve of the gravity induced moment, up to about the maximum moment $M_g(max)$ and thereafter the biasing moment stays substantially constant when bending further;
4. A curve P4 representing a moment diagram in which in a first trajectory the moment rises with the angle $\alpha$ substantially identically to the substantially sinusoidal curve of the gravity induced moment $M_g$, up to about the maximum moment $M_g(max)$ and thereafter the biasing moment M is reduced significantly when bending further, such that upon reaching an angle $\alpha_x$ the moment M biasing the structure 2 back towards the stretched position is so low that it hardly counters further bending and/or squatting of the person.

It is noted that curve P1 represents moments to be at least partly compensated by a or the structure, whereas curves P2, P3 and P4 represent moments compensating at least partly for the moment M exerted by the weight of the upper body bending forward. It is noted that curve P1 represents moments having negative values with respect to the positive values of the moments of curves P2, P3 and P4, but that curve P1 is mirrored in the α-axis for clarity reasons.

In a structure according to the present disclosure the flexibility of the stay or stays 1 or parts 1A, 1B thereof and/or the design of the pivoting provision 50 is preferably such that the moment curve provided thereby acting on a person wearing it, when bending and/or squatting, is according to a curve which is positioned substantially between the third and fourth curve P3 and P4, in order to provide a comfortable support to the person using the structure, which feels safe as well. Preferably the reduction of the moment is not too sudden, i.e. the curve is not too steep directly after reaching $M_g(max)$ in order to prevent the feeling that the support suddenly fails. If the supporting moment M biasing the structure is maintained too high, for example constant at $M_g(max)$ after reaching $M_g(Max)$ as shown in curve P3 then the user could have difficulty bending further or squatting, lifting his legs and the like, since this will then require more muscle force to actually bend the body against said biasing force. The moment M should preferably not be lower than zero, i.e. should preferably always be biasing the structure to the stretched state, clamping the structure onto the body. This can for example be obtained by not having the resilient element 64 cross the pivot axis 60.

In a further preferred embodiment the biasing moment from $M_g(max)$ stays relatively close to the sinusoidal curve P1, such that the weight of the upper body will aid in further bending, requiring little strength to bend further or to bend back towards the upright body position.

In the curves P3 and P4 as shown the relevant curve rises up to a moment M substantially equal to Mg(max) and then remains at that level (P3) or falls sharply (P4). In such embodiments the structure would counter the moment Mg between an angle of 180 degrees (corresponding to a person standing up straight) and about 90 degrees (the person bending over forward over about 90 degrees) substantially entirely, thus providing for almost a balance for the upper body weight over said trajectory. Obviously by changing the properties of for example the resilient element 64 and/or the lay out of the pivot area 50 and/or the flexibility of the stays 1, or parts thereof these curves can be amended. For example, by changing the position of the stop C away from the axis 60 the moment M remaining after the element 64 has reached the stop C can be amended, whereas for example by changing the position of the ends 65, 66 relative to the pivot axis and/or the stop C the angle $α_1$ can be adjusted, since this will change the angle at which the resilient element 64 will abut the stop C.

It should be noted again that when using two stays 1 and/or two pivots with a resilient element each, the moment M exerted by the structure will be the sum of the moments exerted by each stay and/or pivot arrangement individually.

In preferred embodiments of the disclosure a structure according to any one of FIG. 1-10 is combined with a pivot structure as discussed and disclosed in e.g. FIG. 11-16. In such, especially advantageously, embodiments, the supporting action of the structure can approach the behavior of a human spine relatively well. Preferably, when a user bends forward from his upright position, first the upper and/or lower stay part(s) can flex to some extent until the load on the pivot arrangement has increased to such extent that the structure starts to pivot about said pivot arrangement. This may facilitate that the bending and/or supporting action of the structure can approach the behavior of a human spine relatively well. Besides, this can also ease a user to bend to such extent that said user can pick up something from the floor.

In such embodiments, in which a structure according to any one of FIG. 1-10 is combined with a pivot structure as discussed and disclosed in e.g. FIG. 11-16, the stay or stays 1 are flexible and the pivot arrangements 50 allow relative rotation of an upper part 1A relative to a lower part 1B of a stay 1, such that the combined structure 2 provides for an optimal curve representing the biasing moment M urging the structure back to the stretched position in relation to the angle α representing the bending of the body 4 at the hips. Such curve preferably shows a first part in which the moment M rises substantially proportional with and more preferably substantially similar to the moment Mg exerted by the weight of the upper body when bending the body at the hips, and in a second part of the curve the moment drops relatively quickly to allow further bending and/or squatting of the body with limited to no resistance of the structure, but maintaining the structure to be clamped to the body.

In a structure 2 according to the present disclosure the chest support(s), lumbar support(s) and thigh support(s) can move relative to each other such that upon bending of the body of a person wearing the structure 2, relatively little to no movement of the supports 8, 9, 10 is necessary, especially very little to no translations. Preferably the supports provide some freedom of rotation thereof relative to the stay(s), in order to accommodate some angular displacement of the supports.

FIG. 18 is a schematic diagram showing a lower back area moment curve 90 for a person bending over with a structure 2 according to an aspect of the invention and a lower back area moment curve 91 for a person bending over without such structure 2. The X-axis shows the time as a percentage of a movement cycle of a test subject bending forward, waiting in the bent position and then moving back to the upright position. The Y-axis represents the value of the moment on the lower back of the test subject. Both curves 90, 91 show a person starting in an upright position at 0 seconds, who then starts to bend over towards a position in which the upper body part is bent to such extent that the sternum encloses an angle of substantially 90° with the upper legs of said person, whereas the angle between the sternum and the upper legs is about 0° when the person stands upright. The substantial horizontal parts of the curves correspond with said position of the test subject in which said angle is substantially 90°. At the end of the horizontal parts of the curves (at about 70%), the user bent back to its upright position. As can be seen when comparing both curves 90, 91, the maximum moments M are substantially equal with or without the use of a structure. However, in the bent over state, the static load on the user is significantly lower when wearing the structure 2 of the present invention than without said structure. As a result, the user can work longer in a bent over state and/or may experience less strains in his (lower) back.

FIG. 19 shows an alternative embodiment of a structure 2 according to an aspect of the present disclosure, which comprises a substantially rigid arm 70 attached to the at least one stay. For example, as shown here, the structure 2 can comprise two of such arms 70. For example, the structure 2 can comprise a first substantially rigid arm 70 attached to a left stay 1 and as second substantially rigid arm 70 attached to a right stay 1. In embodiments, said arm 70 can be connected to un upper part of the stay. The arm is positioned such as to be directed toward the spinal column of a user during use. The lumbar support 10 is connected to the stay 1 at least partly by being connected to said substantially rigid arm 70. For example, said lumbar support 10 can be connected to a left and a right arm 70. However, in alternative embodiments, both arms 70 may be provided with separated lumbar supports. Alternatively or additionally, the two arms 70 may be integrated into a single arm interconnecting the left and stay the right stay. However, in preferred embodiments said two arms are not rigidly interconnected or integrated, such that it can be made possible to adjust the width of the frame relatively easily.

Due to the at least one substantially rigid arm 70, seen in lateral direction of the user, the lumbar support 10 may at least partly be or become positioned relatively close to the spinal column. Said arm 70 can connect the lumbar support 10 to the stay 1 in a manner that can counteract that the stay 1 twists off the user relatively easily during use.

As further can be seen in the exemplary embodiment of FIG. 19, the structure 2 can further comprise a buttock band 71. Said buttock band 71 can be arranged to extend below a user's buttock or gluteals during use. The buttock band can for instance be arranged to engage with the gluteofemoral fold when a user bends forward relatively far. Thereby, it may be counteracted that the structure and/or its frame moves upwardly when said frame is bent relatively far. Preferably, the buttock band 71 can be interconnecting a left lower stay part with a right lower stay part. It is noted that the buttock band 71 can preferably be arranged to be tightened and loosened such as to be adapted to a user's preferences and/or dimensions. Preferably, the buttock band 71 is worn under the buttocks, more preferably in such a manner that said band is not tightened under the buttocks while the person is standing upright, such as to counter that a user will feel constricted or uncomfortable by said buttock band.

Alternatively or additionally, as can be seen in the exemplary embodiment of FIG. 19, a structure according to any aspect of the present disclosure, may further comprise one or more shoulder bands 72 or braces 72. Preferably, said bands or braces can be substantially flexible and/or can at least partly be formed by means of an elastic band. The one or more shoulder bands 72 or braces 72 may counteract sliding down of the structure 2. In embodiments, a first end 73 of the band 72 is connected to a part of the structure 2 near the chest area, e.g. connected to a chest support or to a part of the stay near the chest support 8, and a second end 74 of the respective band or braces is connected to a part of the stay near the lumbar area, e.g. connected to the lumbar support 10 or to a part of the stay 1 near the lumbar support 10.

In embodiments, such as the embodiment shown in FIG. 19, the structure 2 has at least one pivoting arrangement that comprises biasing means 62 arranged such that during use the upper and lower stay parts 1A, 1B are biased towards a stretched state corresponding with an upright position of a human body, as discussed before. Here, the biasing means 62 comprise a compression spring 75 or a gas spring 75 mounted to one of the lower stay part 1B and the upper stay part 1A. Said compression spring 75 or gas spring 75, which can preferably have a substantially linear spring characteristic, cooperates with a cam surface 76 which is provided at the other one of the lower stay part and the upper stay part. For example, a piston rod 75*a* can therefore be provided with a roller 75 that can cooperate with said cam surface 76. The cooperating cam surface 76 and gas spring 75 are arranged such that when the upper and lower stay parts are pivoted around the pivot axis 60 from a stretched position towards a position including a first angle, the biasing means 62 provide for an increasing biasing moment which biases the stay back to the stretched position and when pivoting further around said pivot axis from the said angle the biasing moment is substantially maintained or decreases.

Although said cam surface 76 can be formed in many different ways, e.g. depending on the spring characteristics of the compression spring 75 or the gas spring 75, an exemplary embodiment of a cam element 77 defining such a cam surface 76 is shown in FIG. 20.

It is noted that the structure 2 may be a modular structure, e.g. including interchangeable parts or elements, in order to adapt the structure to the dimensions and/or preferences of a user thereof. For example, the cam element 77 may be a replaceable part of the wearable structure 2. In such case, the support characteristics of the structure 2 may be adapted relatively easily.

As can for instance be seen in FIGS. 6-8 and FIG. 19, the chest support(s) 8 or chest pad(s) can extend up to and preferably beyond an upper end of the stay 1 and/or above the upper stay part 1A. When the frame and/or stay(s) do not or not substantially extend above the chest support(s) 8 or chest pad(s), it can be facilitated that the one or more stays extend below the armpits, thereby offering relatively a lot of freedom of movement to the user of the wearable structure 2.

It is noted that, for instance in the embodiment of FIG. 19, the upper stay part 1A and/or the lower stay part 1B can be relatively flexible, such that during use, when worn by a person, upon pivoting of the upper stay part 1A relative to the lower stay part 1B, at least one of said stay parts 1A, 1B deforms resiliently. As a result, the deformation of the stay part, especially the upper stay part 1A, can at least to some extent follow the changing shape of the spine of a user of the structure 2.

By arranging the structure 2 such that the at least one stay 1 extends alongside the body or such that two stays 1 extend alongside opposite sides of the body, the structure 2 can be relatively advantageous. This will be elucidated with reference to FIGS. 21A-21C, which each show schematic side views of a skeleton of a user of a wearable structure 2 in both an upright position and in a bent position.

In FIG. 21A, an upper stay 101A is shown that is connected to a pivot 110 in front of the virtual axis of bending of the upper body relative to the legs at the hip/pelvic region. As can be seen when comparing the upright position of the skeleton with the bent over position of the skeleton, relative shortening of the front side of the upper body, e.g. shortening of the distance between the thigh or upper leg 21 and the chest or e.g. shortening of the distance 120, 119 between the pivot 110 and the desired position of the chest support 108, 118, occurs. As can be seen, this will in such cases cause that the upper stay 101A or/or a chest support 108 of a structure extending at the front side of a human body can unwillingly slide upwardly towards a user's neck or throat.

However, in case of an inventive structure 2 of which the stay 1 or stays 1 or at least a stay part, preferably an upper stay part 1A, extends alongside the body, as can be seen in FIG. 21*c*, it can be counteracted that upper parts of the structure 2, e.g. a chest support 8, will slide upwardly. For instance, because it can be facilitated that the stay 1 or respective stay part can substantially follow the movement and/or (changing) shape of the spinal column.

As can be seen in FIG. 21*b*, the length 115, 116 of the upper body can lengthen at the back side of a human body when the person bends over. When a stay of the structure would be provided at the back of a person, and thus not at alongside the body, i.e. along a respective side of the body, a chest support attached thereto would thus slide downwardly unintentionally. Moreover, the structure could unwillingly pull at the shoulder(s) of the user when he is bent over or, in order to counteract such pulling, said structure could need to be designed such as to run relatively high above one's shoulders, at least in a position in which the user stands upright. However, in such relatively high design of the structure, said structure could easily limit the freedom of motion of the user unwillingly.

The invention also relates to the use of a wearable support structure, especially a structure according to one of the embodiments disclosed herein, wherein a chest support of said structure bears at least partly upon a chest area, preferably at least partly upon one or more ribs, wherein a lumbar support of said structure bears upon a lumbar area, preferably at least partly upon one or more lumbar vertebrae and/or at least partly upon the pelvis, e.g. hip bones thereof, and wherein a thigh support of said structure bears upon a front side of a thigh area, preferably wherein a second thigh support of said structure bears upon a front side of a second thigh area.

The invention is by no means limited to the embodiments disclosed and/or discussed in this description. These have only been discussed by way of example. Many amendments and changes can be made to these embodiments, including but not limited to all combinations and permutations of features and elements as disclosed. These should also be considered to have been disclosed.

The invention claimed is:

1. A wearable support structure for at least partly relieving a human body during leaning forward or bending over, comprising a frame having at least one stay having at least one upper stay part for support against a torso of a human body and at least one lower stay part for support against an upper leg of a human body, wherein the at least one upper stay part and the at least one lower stay part are pivotably connected to each other about a pivot axis by means of at least one pivoting arrangement provided between the at least one upper stay part and at least one lower stay part wherein the at least one pivoting arrangement is arranged for allowing pivoting of the at least one upper stay part and at least one lower stay part with respect to each other around the pivot axis from a stretched position to a position including a first angle, wherein the at least one pivoting arrangement comprises a spring structure being mounted to one of the at least one lower stay part and the at least one upper stay part, wherein the spring structure comprises an engagement element configured for engagingly cooperating with a cam surface provided at the other one of the at least one lower stay part and the at least one upper stay part, wherein the cooperating cam surface and spring structure are arranged such that when the at least one upper stay part and at least one lower stay part are pivoted with respect to each other around the pivot axis from a stretched position to a position including the first angle, the spring structure provides for an increasing biasing moment biasing the at least one upper stay part and at least one lower stay part back to the stretched position and when pivoting further around said pivot axis from the said angle the biasing moment is maintained or decreases, wherein the at least one pivoting arrangement is arranged such that when the at least one upper and lower stay parts are pivoted around the pivot axis from the first angle to a second angle that is further from the stretched position than the first angle, the biasing moment decreases.

2. The wearable support structure according to claim 1, wherein the at least one stay is provided with a chest support for bearing upon a chest area, a lumbar support for bearing upon a lumbar area, and a thigh support for bearing upon a front side of a thigh area, and wherein the wearable support structure is shaped and configured such that during use by a human, the at least one stay extends from the chest support, via the lumbar support towards the thigh support, and extends under an armpit of the human using the wearable support structure.

3. The wearable support structure according to claim 2, wherein the at least one stay provided with said supports is shaped such that said at least one stay is configured to be clamped around the human body so as to be suspended from said body substantially by clamping forces.

4. The wearable support structure according to claim 2, wherein the lumbar support is arranged for bearing upon a lumbar area at least partly located substantially at the back of the human body.

5. The wearable support structure according to claim 2, wherein the thigh support is arranged for bearing at least partly upon an inner side and/or a front side of a thigh, the thigh support comprising a U-shaped bracket for partly surrounding a part of a thigh.

6. The wearable support structure according to claim 2, wherein at least one of the supports is connected to the at least one stay by a pivotable connection, so as to enable the respective support to fit the human body when the at least one stay is bent by pivoting the at least one upper stay part and at least one lower stay part with respect to each other.

7. The wearable support structure according to claim 1, comprising two stays in the form of a left stay and a right stay, the left stay arranged to be worn at a left side of the human body, and the right stay arranged to be worn at a right side of the human body.

8. The wearable support structure according to claim 7, wherein the left stay and the right stay are provided with a respective lumbar support for bearing upon a lumbar area, and wherein the left stay is coupled or releasably couplable to the right stay at a back side of the wearable support structure, at or near the lumbar supports.

9. The wearable support structure according to claim 8 wherein the left and right stays are releasably couplable by means of one or more belts and/or buckles.

10. The wearable support structure according to claim 7 wherein the left stay is coupled or releasably couplable to the right stay at a front side of the wearable support structure, at or near the chest of the human body and/or at or near the waist of the human body.

11. The wearable support structure according to claim 1, wherein the wearable support structure is arranged such that the engagement element moves along the cam surface when the at least one upper and lower stay parts are pivoted with respect to each other around the pivot axis from a stretched position to a position including a first angle and when pivoting further around said pivot axis from the said angle, and wherein the cam surface is shaped such as to define that a distance between the pivot axis and a current position at the cam surface at which the engagement element is then located increases when the at least one upper and lower stay parts are pivoted with respect to each other around the pivot axis from the stretched position to the position including the first angle, and wherein the cam surface is further shaped such as to define that said distance between the pivot axis and the current position at the cam surface at which the engagement element is then located is maintained or decreases when pivoting the at least one upper and lower stay parts further around said pivot axis from the said first angle.

12. The wearable support structure according to claim 11, wherein the spring structure comprises a spring element and a separately formed engagement element arranged to cooperate with the cam surface.

13. The wearable support structure according to claim 12, wherein the engagement element is formed by a roller arranged to cooperate with the cam surface.

14. The wearable support structure according to claim 1, wherein the at least one stay has a curved shape being arranged to fit or follow body curves of the human body and wherein the wearable support structure is arranged such that all parts of the wearable support structure are to be located within 20 cm from the human body during use of the wearable support structure.

15. The wearable support structure according to claim 1, wherein the frame is arranged to keep the shoulders and/or neck portion of the human body free.

16. The wearable support structure according to claim 1, wherein at least a portion of at least one of the upper stay part and the at least one lower stay part is relatively flexible, such that during use when worn by a person, said person can twist his body about a longitudinal axis of said body to at least some extent.

17. The wearable support structure according to claim 1, wherein at least a portion of at least one of the upper stay part and the at least one lower stay part is relatively flexible, such that during use when worn by a person, said person can flex laterally to at least some extent.

18. The wearable support structure according to claim 1, wherein at least a portion of at least one of the upper stay part and the at least one lower stay part is relatively flexible, such that during use when worn by a person, upon pivoting of the at least one upper stay part relative to the at least one lower stay part, at least one of said stay parts deforms resiliently.

19. The wearable support structure according to claim 1, wherein the spring structure comprises a gas spring.

20. The wearable support structure according to claim 1, further comprising one or more shoulder bands or braces for counteracting sliding down of the wearable support structure, wherein a first end of the one or more shoulder bands or braces is connected to a part of the wearable support structure near the chest area and a second end of the one or more bands or braces is connected to a part of the stay near the lumbar area.

21. The wearable support structure according to claim 1, further comprising a coat arranged to substantially cover at least the frame.

22. The wearable support structure according to claim 1, further comprising a substantially rigid arm attached to the at least one stay, wherein the arm, when seen in lateral direction of the user, is during use directed toward the spinal column of a user.

23. The wearable support structure according to claim 1, further comprising a buttock band arranged to extend below a user's buttock during use, to counteract upward movement of the frame moves.

24. The wearable support structure according to claim 1, wherein the pivoting arrangement is configured to be positioned in a location next to the hip of the person wearing the wearable support structure during use, wherein the pivot axis of said pivoting arrangement extends substantially through the virtual axis of bending of the upper body relative to the legs at the hip/pelvic region, wherein the wearable support structure is arranged to enable switching said pivoting arrangement from a free state in which the two parts of the at least one stay are configured to be substantially freely pivoted with respect to each other about the pivot axis to a working state in which the two parts of the stay are coupled in a stretched state corresponding with an upright position of a human body when being unloaded, and that further is arranged to be biased back to said stretched state when being bent into a bent state corresponding with a forward leaning position of a human body.

25. A wearable support structure for at least partly relieving a human body during leaning forward or bending over, comprising a frame including at least one stay, the at least one stay having at least one upper stay part for support against a torso of a human body and at least one lower stay part for support against an upper leg of a human body, wherein the at least one upper stay part and the at least one lower stay part are pivotably connected to each other, wherein between the at least one upper stay part and the at least one lower stay part at least one pivoting arrangement is provided, wherein the pivoting arrangement comprises a resilient element connected to the at least one upper stay part and the at least one lower stay part spaced apart from a pivot axis between the at least one upper stay part and at least one lower stay part, the at least one pivoting arrangement being arranged such that when the at least one upper stay part and the at least one lower stay part are pivoted around the pivot axis from a stretched position to a position including a first angle, the resilient element provides for an increasing biasing moment biasing the at least one upper stay part and at least one lower stay part back to the stretched position and when pivoting further around said pivot axis from the said first angle the biasing moment is maintained or decreases, wherein the at least one pivoting arrangement is arranged such that when the at least one upper and lower stay parts are pivoted around the pivot axis from the first angle to a second angle that is further from the stretched position than the first angle, the biasing moment decreases.

26. The wearable support structure according to claim 25, wherein the resilient element comprises at least one elongated spring element, the elongated spring element having a first distal end attached to the at least one upper stay part and a second distal end attached to the at least one lower stay part.

27. The wearable support structure according to claim 26, wherein said spring element is substantially working in a plane parallel to a sagittal plane off a person wearing the wearable support structure.

28. The wearable support structure according to claim 26, wherein a longitudinal direction of said spring element is substantially transverse to the axis of rotation of a hip joint of the human body bending over, and wherein, at least in a stretched state of the wearable support structure corresponding with an upright position of the human body, said spring element is spaced away from said axis and/or from a pivoting point or area where the at least one upper and lower stay parts pivot with respect to each other over at least 15 mm.

29. The wearable support structure according to claim 25, wherein the resilient element has opposite ends connected to the at least one upper stay part and the at least one lower stay part, and wherein the wearable support structure is arranged such that an intermediate part of the resilient element located between distal ends of said resilient element moves from an initial location spaced apart from the pivot axis towards a second location nearer to the pivot axis, such that said intermediate part approaches the pivot axis when the wearable support structure is bent from the stretched state of the wearable support structure towards a bent state corresponding with a forward leaning position of the human body, thereby reducing the component of the moment provided for by the resilient element.

30. The wearable support structure according to claim 29, wherein the pivoting arrangement is configured to be positioned at a location next to the hip of the person wearing the wearable support structure during use such that the pivot axis of said pivot extends substantially through the virtual axis of bending of the upper body relative to the legs at the hip/pelvic region, wherein said pivoting arrangement is provided with a lock for locking the pivoting arrangement in a working state in which the two stay parts are biased with respect to each other such that when the upper and lower stay parts are pivoted around the pivot axis from a stretched position to a position including a first angle, the resilient element provides for an increasing biasing moment biasing the stay back to the stretched position and when pivoting further around said pivot axis from the said angle the biasing moment is maintained or decreases, and wherein the lock is configured to be unlocked to bring the pivoting arrangement into a free state in which the upper and the lower stay parts pivot substantially freely with respect to each other.

31. The wearable support structure according to claim 25, wherein the resilient element has opposite ends connected to the at least one upper stay part and the at least one lower stay part, and an intermediate part, wherein the pivoting arrangement comprises a stop, wherein the intermediate part is spaced apart from the stop in the stretched position of the stay, and wherein the wearable support structure is arranged such that said intermediate part abuts against said stop when pivoting the at least one upper stay part relative to the at least one lower stay part, such that when the at least one upper stay part is pivoted further relative to the at least one lower stay part, the resilient element is bent around the stop, wherein the wearable support structure is arranged such that the intermediate part approaches the stop when the at least one upper stay part and the at least one lower stay part are pivoted from the stretched position towards a bent state corresponding with a forward leaning position of the human body.

32. The wearable support structure according to claim 25, wherein the resilient element of the at least one pivoting arrangement comprises a spring being mounted to one of the at least one lower stay part and the at least one upper stay part and cooperating with a cam surface provided at the other one of the at least one lower stay part and the at least one upper stay part, wherein the cooperating cam surface and spring are arranged such that when the at least one upper stay part and the at least one lower stay part are pivoted around the pivot axis from a stretched position to a position including a first angle, the resilient element providing for an increasing biasing moment biasing the stay back to the stretched position and when pivoting further around said pivot axis from the said angle the biasing moment is maintained or decreases.

33. The wearable support structure according to claim 25, wherein the wearable support structure is arranged such that the at least one upper stay part and the at least one lower stay part are configured to pivot with respect to each other at or near an axis of rotation of a hip joint of a human body bending over.

34. The wearable support structure according to claim 25, wherein at least a portion of at least one of the at least one upper stay part and the at least one lower stay part is relatively flexible, such that during use when worn by a person, upon pivoting of the at least one upper stay part relative to the at least one lower stay part, at least a portion of at least one of said stay parts deforms resiliently.

35. The wearable support structure according to claim 25, wherein at least a lower part of the at least one upper stay part and at least an upper part of the at least one lower stay part are arranged to be positioned at a side of the human body, wherein the lower part of the at least one upper stay part and the upper part of the at least one lower stay part are provided with cooperating pivoting arrangements forming a hinge, and wherein during use are configured to be positioned aside a human hip at or near the axis of rotation of a hip joint of a human body bending over.

36. The wearable support structure according to claim 25, wherein the wearable support structure is shaped and arranged such that the wearable support structure can be clamped around the human body so as to be suspended from said body substantially by clamping forces exerted by deformation of each stay and/or the or each resilient element.

37. The wearable support structure according to claim 25, wherein at least a portion of at least one of the upper and/or at least a portion of the at least one lower stay part is flexible, and wherein the wearable support structure is configured to be clamped around the human body at least partly by biasing the at least one upper and/or lower stay parts such that a chest support for bearing upon a chest area provided at the at least one upper stay part is biased toward the chest area during use, a lumbar support for bearing upon a lumbar area provided at the at least one upper stay part is biased toward the lumbar area during use, and/or a thigh support for bearing upon a front side of a thigh area is biased toward the front side of the thigh area during use.

38. The wearable support structure according to claim 25, wherein the resilient element comprises a non-linear spring element configured to exert a certain force F when elongated over a first distance X and exert a force smaller than twice the force F when elongated over a second distance being twice as large as the first distance X.

39. The wearable support structure according to claim 25, comprising two upper stay parts and two lower stay parts in the form of a left upper stay part, a right upper stay part, a left lower stay part and a right lower stay part, the left upper stay part and the left lower stay part arranged to be worn at a left side of the human body, and the right upper stay part and the right lower stay part arranged to be worn at a right side of the human body.

40. The wearable support structure according to claim 25, wherein the upper stay is arranged to be fixedly attached to the torso and/or the lower stay is arranged to be fixedly attached to the upper leg using one or more straps for strapping said stay to the respective body part.

41. A wearable support structure for at least partly relieving a human body during leaning forward or bending over, comprising a frame having at least one upper stay part for support against a torso of a human body and at least one lower stay part for support against an upper leg of a human body, wherein the at least one upper stay part and the at least one lower stay part are pivotably connected to each other, wherein between the at least one upper and lower stay parts at least one pivoting arrangement is provided, wherein the pivoting arrangement comprises a resilient element and is arranged such that when the at least one upper and lower stay parts are pivoted around the pivot axis from a stretched position to a position including a first angle, the resilient element provides for a biasing moment biasing the stay back to the stretched position, wherein the at least one upper stay part or the at least one lower stay part comprises an additional pivoting arrangement for pivoting two parts of the respective stay part with respect to each other, wherein the additional pivot arrangement is configured to be positioned in a location next to and/or near to the hip of the person wearing the wearable support structure during use, wherein the additional pivoting arrangement is lockable and configured to be switchable between a free state in which the two parts of the respective stay part can substantially freely pivot with respect to each other and a working state in which the two parts of the respective stay part are coupled to form a combined stay part substantially behaving as a single stay part, wherein the at least one pivoting arrangement is arranged such that when the at least one upper and lower stay parts are pivoted around the pivot axis from the first angle to a second angle that is further from the stretched position than the first angle, the biasing moment decreases.

42. A method of using the wearable support structure according to claim 1, the method comprising: wearing the wearable support structure with the chest support bearing at least partly upon one or more ribs, the lumbar support bearing at least partly upon one or more lumbar vertebrae and/or at least partly upon the pelvis, and the thigh support bearing upon a front side of a thigh area of the human body.

\* \* \* \* \*